United States Patent
Liao et al.

(10) Patent No.: US 11,654,122 B2
(45) Date of Patent: May 23, 2023

(54) SYSTEMS, METHODS, AND KITS FOR ALTERING THE COLOR OF THE HAIR

(71) Applicant: L'Oreal, Paris (FR)

(72) Inventors: Zhengzheng Liao, Cranford, NJ (US); Martin Asare, Springfield, NJ (US); Guojin Zhang, Westfield, NJ (US); Sivaramakrishnan Muthukrishnan, Bridgewater, NJ (US); Aakash Jagat Parekh, Edison, NJ (US); Yuri Lvov, Ruston, LA (US)

(73) Assignee: L'OREAL, Paris (FR)

( * ) Notice: Subject to any disclaimer, the term of this patent is extended or adjusted under 35 U.S.C. 154(b) by 0 days.

(21) Appl. No.: 17/219,868

(22) Filed: Mar. 31, 2021

(65) Prior Publication Data

US 2022/0323382 A1    Oct. 13, 2022

(51) Int. Cl.
*A61Q 5/10* (2006.01)
*A61K 31/14* (2006.01)
*A61Q 5/06* (2006.01)

(52) U.S. Cl.
CPC .............. *A61K 31/14* (2013.01); *A61Q 5/065* (2013.01); *A61K 2800/884* (2013.01)

(58) Field of Classification Search
CPC .... A61Q 5/10; A61Q 5/065; A61K 2800/884; A61K 8/416; A61K 8/26; A61K 8/02; A61K 2800/432
USPC .......................................................... 8/405
See application file for complete search history.

(56) References Cited

U.S. PATENT DOCUMENTS

| | | | |
|---|---|---|---|
| 7,691,398 B2 | 4/2010 | Arai et al. | |
| 8,507,056 B2 | 8/2013 | Lvov et al. | |
| 10,166,175 B1* | 1/2019 | Lvov ........................ | A61Q 5/10 |
| 10,398,635 B1* | 9/2019 | Elsen-Wahrer .......... | A61K 8/22 |
| 10,799,439 B2* | 10/2020 | Lvov ...................... | A01N 47/16 |
| 2019/0060196 A1* | 2/2019 | Elsen ....................... | A61K 8/22 |
| 2020/0078278 A1 | 3/2020 | Lvov et al. | |

FOREIGN PATENT DOCUMENTS

| | | |
|---|---|---|
| FR | 2940095 A1 | 6/2010 |
| KR | 10-1943523 B1 | 1/2019 |
| WO | 2013/150268 A2 | 10/2013 |

OTHER PUBLICATIONS

Abdullayev, et al., "Halloysite clay nanotubes as a ceramic "skelton" for functional biopolymer composites with sustained drug release," Journal of Materials Chemistry B, DOI: 10.1039/c3tb20059k, downloaded by Brigham Young University on Apr. 26, 2013, published on Apr. 4, 2013, on http://pubs.rsc.org, pp. 2894-2903.

(Continued)

*Primary Examiner* — Eisa B Elhilo
(74) *Attorney, Agent, or Firm* — The Marbury Law Group, PLLC

(57) ABSTRACT

The disclosure relates to systems for altering the color of the hair, comprising a pretreatment composition comprising at least one cationic surfactant and a dyeing composition comprising at least one microtube-dye composite. The disclosure also relates to methods of altering the color of the hair using the systems, as well as kits comprising the systems.

23 Claims, 6 Drawing Sheets

4E  4A  4B  4C  4D

(56) References Cited

OTHER PUBLICATIONS

"Cattier Coloration à L'Argile Capillaire 1.0 noir," (Semi-Permanent Colouring Hair Care with Clay), retrieved from the internet: https://www.cattier-paris.com/fr/cooration-capillaire-a-l-argile-1-0-noir-to10.html, [Apr. 12, 2021].
Cavallaro, et al., "Hydrophobically Modified Halloysite Nanotubes as Reverse Micelles for Water-in-Oil Emulsion," Langmuir, American Chemical Society, https://doi.org/10.1021/acs.langmuir. 5b01181, Jun. 26, 2015, pp. A-G.
"Garnier Hair Color Color Styler Intense Wash-Out Color, Blue Burst," Garnier, retrieved from the Internet: https://www.amazon.com/Garnier-Color-Styler-Intense-Wash-Out/dp/B00NA2YJDO [Apr. 12, 2021].
Garnier, "Garnier Hair Color Express Retouch Gray Hair Concealer, Instant Gray Coverage, Brown, 1 Count," retrieved from Internet: https://www.amazon.com/Garnier-Express-Retouch-Concealer-Coverage/dp/B07KJZFW21, [Apr. 12, 2021].
French Search Report and Written Opinion for counterpart FR Application No. 2108206, dated Apr. 12, 2022.
Santos et al., "Evolution of Hair Treatment and Care: Prospects of Nanotube-Based Formulations," Nanomaterials, vol. 9, No. 6, XP055912001, Jun. 21, 2019, p. 903.
Panchal et al., "Self-assembly of clay nanotubes on hair surface for medical and cosmetic formulations," Nanoscale, vol. 10, No. 38, XP055912034, Oct. 4, 20198, pp. 18205-18216.
Copending U.S. Appl. No. 17/841,290, "Systems, Methods, and Kits for Altering the Color of the Hair," Inventor: aakash Parekh, filed Jun. 15, 2022.
Non-Final Office Action for copending U.S. Appl. No. 17/841,290, dated Mar. 20, 2023.

\* cited by examiner

SYSTEMS, METHODS, AND KITS FOR ALTERING THE COLOR OF THE HAIR

TECHNICAL FIELD

The present disclosure relates to systems, methods, and kits for altering the color of the hair.

BACKGROUND

Consumers desire to use cosmetic compositions to enhance the appearance of keratinous substrates such as hair, e.g., by changing the color, style, and/or shape of the hair, and/or by imparting various properties to hair, such as shine and conditioning. Many of the known compositions and processes for enhancing the appearance of the hair involve chemical treatment of the hair. For example, the process of altering the color of hair can involve dyeing the hair by depositing an artificial color onto the hair which provides a different shade or color to the hair.

Traditional hair dyeing processes include permanent and semi-permanent or temporary hair dyeing. Permanent hair dyeing compositions uses oxidation dye precursors, which are also known as primary intermediates or couplers. These oxidation dye precursors are colorless or weakly colored compounds which, when combined with oxidizing products, give rise to colored complexes by a process of oxidative condensation. The permanent hair dye compositions also contain ammonia or other alkalizing agents which causes the hair shaft to swell, thus allowing the small oxidative dye molecules to penetrate the cuticle and cortex before the oxidation condensation process is completed. The resulting larger-sized colored complexes from the oxidative reaction are then trapped inside the hair fiber, thereby permanently altering the color of the hair. On the other hand, semi-permanent or temporary hair dyeing compositions typically use pigments, liposoluble dyes, natural dyes, or direct dyes chosen from acidic (anionic), basic (cationic), or neutral direct dyes which are deposited onto the hair fiber to impart color to the hair.

It is known that traditional hair coloring compositions have drawbacks, however. For example, oxidative hair dyeing processes typically cause damage to the hair such as breakage, dryness, roughness, and/or brittleness, and/or scalp or skin irritation due to the use of hydrogen peroxide and alkaline agents required to achieve the permanent coloration of the hair fibers.

Semi-permanent or temporary hair dye compositions may provide chromatic color to the hair, but the color may lack persistence due to the nature of the interactions that bind the direct dyes to the hair fiber and/or light-sensitivity. In addition, semi-permanent or temporary hair dye compositions may also cause skin and/or scalp irritation. Additionally, semi-permanent or temporary hair dyes typically are not able to provide the same vibrancy or diversity of shades as permanent hair dye compositions.

It was previously discovered that alumino-silicate microtubes could be used as a carrier for synthetic or natural dyes, for example as described in U.S. Pat. No. 10,799,439. However, although this microtube-dye composite can be used to provide color to hair in a manner that does not cause damage to the hair or skin and/or scalp irritation, the process may lead to unsatisfactory color deposition and hair coloring efficiency. In addition, the hair color may not persist through several shampoos.

The present inventors have now surprisingly discovered methods for coloring hair using a microtube-dye composite which provides enhanced color deposition and more vibrant hair colors, while retaining the benefits of less hair damage and skin and/or scalp irritation.

SUMMARY

It has been surprisingly and unexpectedly found that systems, methods, and kits for altering the color of the hair according to the disclosure can provide stronger, more vibrant color to the hair, and which have the advantage of reduced damage to the hair relative to traditional hair coloring processes.

In one embodiment, the disclosure relates to systems for altering the color of the hair comprising (a) a pretreatment composition comprising at least one cationic surfactant and at least one solvent, and (b) a dyeing composition comprising at least one microtube-dye composite and at least one solvent, wherein, in the microtube-dye composite, the dye comprises at least one anionic or neutral hair dyeing agent.

In various embodiments, the at least one cationic surfactant in the pretreatment compositions may be chosen from quaternary ammonium salts of formula (I):

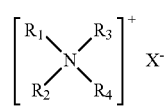

wherein R1 to R4, which may be identical or different, are chosen from a linear or branched aliphatic group comprising from 1 to 30 carbon atoms or an aromatic group, wherein at least one of the groups R1 to R4 comprise from 12 to 22 carbon atoms, and $X^-$ is an anionic counterion chosen from halides. In preferred embodiments, the at least one cationic surfactant is chosen from alkyltrimethylammonium chlorides in which the alkyl group contains from 12 to 22 carbon atoms, such as behenyltrimethylammonium chloride (behentrimonium chloride), distearyldimethylammonium chloride, cetyltrimethylammonium chloride (cetrimonium chloride), benzyldimethylstearylammonium chloride, hydroxyethyl oleyldimethylammonium chloride, dodecyltrimethylammonium chloride, dodecyltrimethylammonium bromide, dicetyldimonium chloride, ditallow dimethyl ammonium chloride, or a mixture thereof.

The pretreatment compositions in systems according to the disclosure may be aqueous compositions, and may comprise one or more cationic surfactants in an amount ranging from about 0.001% to about 25%, such as about 0.01% to about 10%, or about 0.1% to about 5% by weight, relative to the total weight of the pretreatment composition.

In various embodiments, the dyeing compositions in systems according to the disclosure comprise microtube-dye composites chosen from halloysite-dye composites comprising at least one anionic or neutral hair dyeing agent. For example, the at least one anionic or neutral hair dyeing agent may be chosen from acidic nitro direct dyes, acidic azo dyes, acidic azine dyes, acidic triarylmethane dyes, acidic indoamine dyes, acidic anthraquinone dyes, indigoid dyes, natural dyes, or combinations thereof.

The dyeing composition in systems according to the disclosure may be aqueous compositions, and may comprise one or more microtube-dye composites, e.g. one or more halloysite-dye composites, in an amount ranging from about 0.01% to about 15%, such as about 0.1% to about 10%, or about 0.1% to about 5% by weight, relative to the total weight of the dyeing composition.

In a further embodiment, the disclosure relates to methods of altering the color of the hair by treating the hair with the systems described herein.

For example, in various embodiments, the methods comprise (a) applying a pretreatment composition described herein to the hair, optionally leaving the pretreatment composition on the hair for a leave-in period, such as from about 30 seconds to about 5 minutes, optionally removing all or substantially all of the pretreatment composition from the hair, e.g. by rinsing and/or towel-drying the hair, and (b) applying a dyeing composition described to the hair, leaving the dyeing composition on the hair for a leave-in period, such as from about 1 minute to about 45 minutes, and rinsing the dyeing composition from the hair.

In a still further embodiment, the disclosure relates to kits comprising the systems described herein.

For example, in one embodiment, the kit is a multi-compartment kit comprising a first compartment comprising a pretreatment composition comprising at least one cationic surfactant, and a second compartment comprising a dyeing composition comprising at least one microtube-dye composite, wherein, in the microtube-dye composite, the dye comprises at least one anionic or neutral hair dyeing agent.

In various embodiments, the pretreatment composition in the first compartment may comprise at least one cationic surfactant chosen from quaternary ammonium salts of formula (I):

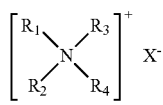

(I)

wherein R1 to R4, which may be identical or different, are chosen from a linear or branched aliphatic group comprising from 1 to 30 carbon atoms or an aromatic group, wherein at least one of the groups R1 to R4 comprise from 12 to 22 carbon atoms, and X⁻ is an anionic counterion chosen from halides. In preferred embodiments, the at least one cationic surfactant is chosen from alkyltrimethylammonium chlorides in which the alkyl group contains from 12 to 22 carbon atoms, such as behenyltrimethylammonium chloride, distearyldimethylammonium chloride, cetyltrimethylammonium chloride, benzyldimethylstearylammonium chloride, hydroxyethyl oleyldimethylammonium chloride, dodecyltrimethylammonium chloride, dodecyltrimethylammonium bromide, dicetyldimonium chloride, or a mixture thereof.

The pretreatment composition in the first compartment may be an aqueous composition, and may comprise one or more cationic surfactants in an amount ranging from about 0.001% to about 25%, such as about 0.01% to about 10%, or about 0.1% to about 5% by weight, relative to the total weight of the pretreatment composition.

In various embodiments, the dyeing compositions in the second compartment comprise microtube-dye composites, e.g. halloysite-dye composites, comprising at least one anionic or neutral hair dyeing agent. For example, the at least one anionic or neutral hair dyeing agent may be chosen from acidic nitro direct dyes, acidic azo dyes, acidic azine dyes, acidic triarylmethane dyes, acidic indoamine dyes, acidic anthraquinone dyes, indigoid dyes, natural dyes, or combinations thereof.

The dyeing composition in the second compartment may be an aqueous composition, and may comprise one or more microtube-dye composites, e.g. one or more halloysite-dye composites, in an amount ranging from about 0.01% to about 15%, such as about 0.1% to about 10%, or about 0.1% to about 5% by weight, relative to the total weight of the dyeing composition.

DETAILED DESCRIPTION

Figure 1:
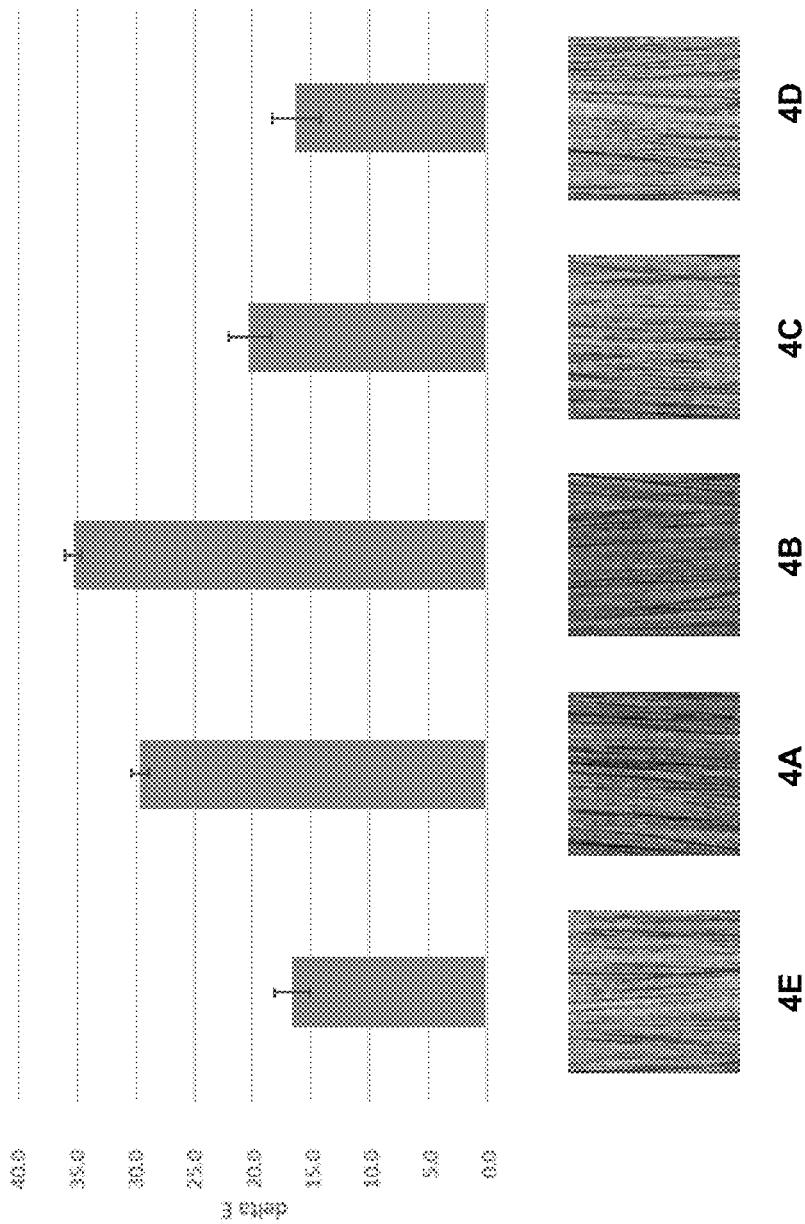
FIG. 1 is a graph demonstrating change in ΔE of hair treated according to methods of the disclosure with pretreatment compositions comprising cationic surfactants followed by dyeing compositions comprising microtube-dye composites, compared to hair treated with comparative methods, where Example 4B, having hair pretreated with a composition comprising cetyltrimethylammonium chloride followed by dyeing the hair with the halloysite-acid red 33 composite, showed the greatest enhancement in color deposition and vibrancy.

The disclosure relates to systems, methods, and kits for altering the color of the hair. The systems, methods, and kits according to the disclosure surprisingly and unexpectedly provide improved color deposition to the hair that result in more vibrant and satisfying coloration to the hair.

Systems

It has been surprisingly and unexpectedly discovered that when hair is treated with a system comprising a pretreatment composition comprising at least one cationic surfactant, and a dyeing composition comprising a microtube-dye composite, improved color deposition onto the hair and more vibrant hair color can be achieved.

Pretreatment Composition

The systems according to the disclosure comprise at least one pretreatment composition comprising at least one cationic surfactant. Useful cationic surfactants may be chosen from, for example, quaternary ammonium salts of the following formula (I):

in which $R_1$ to $R_4$, which may be identical or different, represent a linear or branched aliphatic group comprising from 1 to 30 carbon atoms or an aromatic group such as aryl or alkylaryl, wherein at least one of the groups $R_1$ to $R_4$ comprise from 12 to 22 carbon atoms, and $X^-$ is an anionic counterion chosen from halides. The aliphatic groups may be chosen from, for example, $C_1$-$C_{30}$ alkyl, $C_1$-$C_{30}$ alkenyl, $C_1$-$C_{30}$ alkoxy, polyoxy($C_2$-$C_6$)alkylene, $C_1$-$C_{30}$ alkylamide, ($C_{12}$-$C_{22}$)alkylamido($C_2$-$C_6$)alkyl, ($C_{12}$-$C_{22}$)alkylacetate, or $C_1$-$C_{30}$ hydroxyalkyl.

By way of non-limiting example, tetraalkylammonium halides such as alkyltrimethylammonium halides may be chosen. For example, dialkyldimethylammonium or alkyltrimethylammonium chlorides in which the alkyl group(s) contains from 12 to 22 carbon atoms, such as from 12 to 20 carbon atoms, from 12 to 18 carbon atoms, or 16 carbon atoms, may be useful in certain embodiments. By way of non-limiting example, behenyltrimethylammonium chloride, distearyldimethylammonium chloride, cetyltrimethylammonium chloride, benzyldimethylstearylammonium chloride, hydroxyethyl oleyldimethylammonium chloride, dodecyltrimethylammonium chloride, dodecyltrimethylammonium bromide, dicetyldimonium chloride, ditallow dimethyl ammonium chloride, or mixtures thereof may be chosen. In a preferred embodiment, cetyltrimethylammonium chloride is chosen.

The total amount of the cationic surfactant may range from about 0.001% to about 25% by weight, relative to the total weight of the pretreatment composition. For example, in some embodiments, the total amount of the cationic surfactant may range from about 0.001% to about 20%, such as about 0.001% to about 15%, about 0.001% to about 10%, 0.001% to about 9%, about 0.001% to about 8%, about 0.001% to about 7%, about 0.001% to about 6%, about 0.001% to about 5%, about 0.001% to about 4%, about 0.001% to about 3%, about 0.001% to about 2.5%, about 0.001% to about 2%, about 0.001% to about 1.5%, about 0.001% to about 1%, about 0.001% to about 0.5%, about 0.01% to about 25%, about 0.01% to about 20%, about 0.01% to about 15%, about 0.01% to about 10%, 0.01% to about 9%, about 0.01% to about 8%, about 0.01% to about 7%, about 0.01% to about 6%, about 0.01% to about 5%, about 0.01% to about 4%, about 0.01% to about 3%, about 0.01% to about 2.5%, about 0.01% to about 2%, about 0.01% to about 1.5%, about 0.01% to about 1%, about 0.01% to about 0.5%, about 0.1% to about 25%, about 0.1% to about 20%, about 0.1% to about 15%, about 0.1% to about 10%, 0.1% to about 9%, about 0.1% to about 8%, about 0.1% to about 7%, about 0.1% to about 6%, about 0.1% to about 5%, about 0.1% to about 4%, about 0.1% to about 3%, about 0.1% to about 2.5%, about 0.1% to about 2%, about 0.1% to about 1.5%, about 0.1% to about 1%, or about 0.1% to about 0.5% by weight, relative to the total weight of the pretreatment composition. In other embodiments, the total amount of the cationic surfactant ranges from about 0.2% to about 25%, about 0.2% to about 20%, about 0.2% to about 15%, about 0.2% to about 10%, about 0.2% to about 9%, about 0.2% to about 8%, about 0.2% to about 7%, about 0.2% to about 6%, about 0.2% to about 5%, about 0.2% to about 4%, about 0.2% to about 3%, about 0.2% to about 2.5%, about 0.2% to about 2%, about 0.2% to about 1.5%, about 0.2% to about 1%, about 0.5% to about 25%, about 0.5% to about 20%, about 0.5% to about 15%, about 0.5% to about 10%, about 0.5% to about 9%, about 0.5% to about 8%, about 0.5% to about 7%, about 0.5% to about 6%, about 0.5% to about 5%, about 0.5% to about 4%, about 0.5% to about 3%, about 0.5% to about 2.5%, about 0.5% to about 2%, about 0.5% to about 1.5%, or about 0.5% to about 1% by weight, relative to the total weight of the pretreatment composition.

In at least one embodiment, the pretreatment composition comprises less than 5% of surfactants other than cationic surfactants, such as less than 4%, less than 3%, less than 2%, less than 1%, less than 0.5%, less than 0.1%, or less than 0.01%, by weight of the pretreatment composition. In a further embodiment, the pretreatment composition is substantially free of surfactants other than cationic surfactants. In a further embodiment, the pretreatment composition is free of surfactants other than cationic surfactants. In yet a further embodiment, the pretreatment composition is free or substantially free of anionic surfactants.

In another embodiment, if a surfactant other than a cationic surfactant is present, the ratio of cationic surfactant to non-cationic surfactant is greater than 2:1, such as greater than 3:1, greater than 4:1, greater than 5:1, greater than 6:1, greater than 7:1, greater than 8:1, greater than 9:1, greater than 10:1, greater than 20:1, greater than 50:1, or greater than 100:1.

The pretreatment composition optionally comprises at least one solvent, for example water, non-aqueous solvents, or a mixture thereof. In various embodiments, the solvent of the pretreatment composition comprises, consists essentially of, or consists of water.

Exemplary non-aqueous solvents include, for example, glycerin, $C_{1-4}$ alcohols, organic solvents, fatty alcohols, fatty ethers, fatty esters, polyols, glycols, vegetable oils, mineral oils, liposomes, laminar lipid materials, and mixtures thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. The organic solvents can be volatile or non-volatile compounds.

In certain embodiments, the pretreatment composition comprises from about 60% to about 99.999% of a solvent, such as water, by weight. In certain embodiments, the pretreatment composition comprises from about 75% to about 99.999% solvent by weight, such as from about 75% to about 99.99%, about 75% to about 99.9%, about 75% to about 99%, about 75% to about 98%, about 75% to about 97%, about 90% to about 99.9%, about 90% to about 99%, about 90% to about 98%, about 90% to about 97%, about 95% to about 99.9%, about 95% to about 99%, about 95% to about 98%, or about 95% to about 97%, by weight of the pretreatment composition.

The pretreatment composition may comprise additional components, as long as such additional components do not substantially interfere with the cationic nature of the pretreatment composition. By way of example only, the pretreatment composition may comprise pH adjusters, preservatives, humectants, oils, fragrances, etc.

In various embodiments, the pretreatment composition has a pH of less than or equal to 7.

Dyeing Composition

The systems according to the disclosure comprise at least one dyeing composition comprising at least one microtube-dye composite.

The term "microtube" as used herein includes any tubular material having micron level dimensions or less (e.g., the length dimension of the tube being under about 1 mm), including nanotubes, or may refer to tubular structures having an outer diameter that is sub-micron and lengths under about 100 microns, such as under about 50 microns, or under about 10 microns. Various exemplary embodiments employ microtubes which are aluminosilicate in nature, such as halloysite and imogolite, or which are not aluminosilicate in nature, such as sepiolite or cylindrite.

Exemplary and non-limiting microtubes include, for example halloysite ($Al_2Si_2O_5(OH)_4$) microtubes. Halloysite forms as small cylinders (nanotubes) that may, for example, have a wall thickness ranging from about 10 to about 15 atomic aluminosilicate sheets, an outer diameter ranging from about 50 to about 60 nm, an inner diameter ranging from about 12 to about 20 nm, and a length ranging from about 0.5 to about 10 µm, with an average length of about 1 µm. Their outer surface is mostly composed of —Si—O—Si— and the inner surface of —Al—OH, and hence those surfaces are oppositely charged at approximately neutral pH. In various embodiments of the disclosure, the microtubes comprise, consist essentially of, or consist of halloysite.

The microtubes may be "loaded" with a hair dyeing agent, meaning that the dye agent is incorporated into the lumen of the microtube, in order to form the microtube-dye composite. The microtube-dye composite may be formed by methods known for loading microtubes (such as halloysite), for example as described in U.S. Pat. Nos. 8,507,056 and 10,799,439, and Abdullayev E. and Lvov Y., "Halloysite clay nanotubes as a ceramic 'skeleton' for functional biopolymer composites with sustained drug release," *J. Mater. Chem. B*, 1(23):2894-2903 (2013), all of which are incorporated herein by reference.

By way of example, a hair dyeing agent may be dissolved in an appropriate solvent, such as water, a non-aqueous solvent, or a mixture thereof, to form a solution. The amount of dye may be chosen such that it is near or at the solubility limit of the dye in the solvent. In one exemplary embodiment, the solution may contain from about 1% to about 10%, by weight, of the hair dyeing agent. An appropriate amount of the microtube component may be added to the dye solution, for example in powder form, to form a dispersion. The amount of the microtube component may, for example, be chosen to provide a weight ratio of microtube:dye ranging from about 1:1 to about 10:1, such as from about 2:1 to about 5:1.

The dispersion may optionally be homogenized, sonicated, stirred, placed under vacuum, washed, and/or dried to provide microtubes loaded with the hair dyeing agent. For example, the dispersion may be sonicated for a period of time such as about 2-10 minutes, for example about 5 minutes, then mixed for a period of time such as about 10-60 minutes, for example about 30 minutes. The sonication and/or mixing steps can be repeated one or more times, and may be carried out under either ambient conditions, under vacuum and/or elevated temperature, or combinations thereof, until the microtubes are loaded with dye. Once the microtubes are loaded, the supernatant may be removed, e.g. by centrifuging, and the microtube-dye composite can be dried, for example in an oven at a temperature of at least 40° C., such as at least 45° C., for example about 50° C.

In one embodiment, the solvent may comprise, consist essentially of, or consist of water. In further embodiments, the solvent may comprise, consist essentially of, or consist of a non-aqueous solvent. Exemplary and non-limiting non-aqueous solvents that can be used for loading the hair dyeing agent into the microtubes include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbitan, acetine, diacetine, triacetine, sulfolane, acetone, and mixtures thereof.

In certain embodiments, the solvent may comprise both water and a non-aqueous solvent, for example from about 1% to about 99% water mixed with about 1% to about 99% non-aqueous solvent. It is within the ability of those skilled in the art to choose the appropriate solvent and/or combination of solvents, and amounts thereof, in order to dissolve the hair dyeing agents useful according to the disclosure.

In various embodiments, the internal and/or external surface of the microtube may be modified prior to loading with the hair dyeing agent, which may aid dye loading and/or the hair dyeing process. For example, the microtubes may be modified with an anionic surfactant, such as sodium dodecyl sulphate, or may be made hydrophobic, which may be preferred when loading a hydrophobic dye. In one embodiment, the microtubes may be dispersed in a solution of anionic surfactant (e.g. at a weight ratio of about 1:1), optionally stirred and/or centrifuged, and optionally washed and/or dried, in order to produce microtubes modified with the anionic surfactant, having an increased net negative charge relative to unmodified microtubes.

In another embodiment, the microtubes may be made hydrophobic, for example by coupling a silane coupling agent to hydroxyl groups present at the surface of the microtubes to increase the contact angle of the microtube, or by absorption of anionic amphiphile molecules into the positive lumen. In various embodiments, the contact angle may be increased to at least about 30°, such as at least about 50°, at least about 75°, at least about 100°, at least about 115°, such as about 120°. Exemplary and non-limiting silane coupling agents include (3-glycidyloxypropyl) trimethoxy silane (GTMS), 3-aminopropyltriethoxy silane (APTES), hexamethyldisilazane (HMDS), and octadecyltrimethoxy silane (ODTMS). By way of example, the microtubes may be sonicated with the silane coupling agent in a solvent, e.g. water, an organic solvent, or a mixture thereof, followed by refluxing at increased temperature, e.g. greater than about 50° C. or greater than about 75° C., such as about 85° C.

In yet a further embodiment, the surface of the microtube may be selectively etched. For example, the inner surface of the halloysite lumen may be etched by treatment with acid, such as sulfuric acid, which may increase the diameter of the lumen. In one embodiment, the halloysite can be stirred in sulfuric acid (e.g. 1M) at elevated temperature, e.g. greater than about 50° C. or greater than about 75° C., such as about 80° C., for a period of time such as at least 2 hours, at least 4 hours, at least 6 hours, or at least 8 hours. Such treatment can increase the loading capacity of the microtubes by 2, 3, 4, or even more times the pre-etching loading capacity.

Useful hair dyeing agents according to the disclosure include anionic (acidic) and neutral hair dyeing agents.

The term "anionic hair dyeing agent" is intended to mean any hair dyeing agent comprising in its structure at least one $CO_2R$ or $SO_3R$ substituent with R denoting a hydrogen atom or a cation originating from a metal or an amine, or an ammonium ion. By way of example, anionic hair dyeing agents may be chosen from acidic nitro direct dyes, acidic azo dyes, acidic azine dyes, acidic triarylmethane dyes, acidic indoamine dyes, acidic anthraquinone dyes, indigoid dyes, acidic natural dyes, and combinations thereof.

In one exemplary embodiment, the anionic hair dyeing agent may be chosen from the diaryl anionic azo dyes of formula (II) or (III):

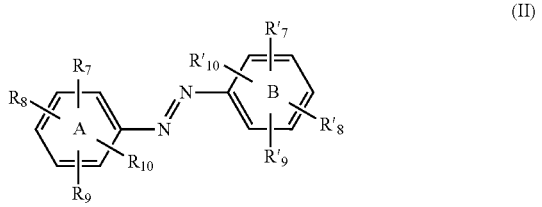

(II)

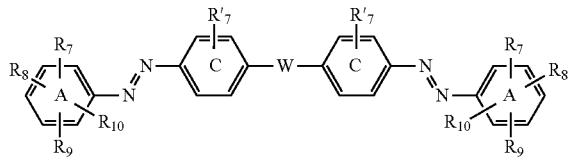

(III)

wherein:
$R_7$, $R_8$, $R_9$, $R_{10}$, $R'_7$, $R'_8$, $R'_9$ and $R'_{10}$, which may be identical or different, represent a hydrogen atom or a group chosen from:
alkyl;
alkoxy, alkylthio;
hydroxyl, mercapto;
nitro, nitroso;
$R°$—C(X)—X'—, $R°$—X'—C(X)—, $R°$—X'—C(X)—X"— with $R°$ representing a hydrogen atom or an alkyl or aryl group; X, X' and X", which may be identical or different, representing an oxygen or sulfur atom, or NR with R representing a hydrogen atom or an alkyl group;
$(O)_2S(O^-)$—, $M^+$ with $M^+$ representing a hydrogen atom or a cationic counterion;
$(O)CO^-$—, $M^+$ with $M^+$ as defined previously;
R"—S(O)₂—, with R" representing a hydrogen atom or an alkyl, aryl, (di)(alkyl)amino or aryl(alkyl)amino group; preferentially a phenylamino or phenyl group;
R'"—S(O)₂—X'— with R'" representing an alkyl or optionally substituted aryl group, X' as defined previously;
(di)(alkyl)amino;
aryl(alkyl)amino optionally substituted with one or more groups chosen from i) nitro; ii) nitroso; iii) $(O)_2S(O^-)$—, $M^+$ and iv) alkoxy, with $M^+$ as defined previously;
optionally substituted heteroaryl; preferentially a benzothiazolyl group;
cycloalkyl; in particular cyclohexyl;
Ar—N═N— with Ar representing an optionally substituted aryl group; preferentially a phenyl optionally substituted with one or more alkyl, $(O)_2S(O^-)$—, $M^+$ or phenylamino groups; or
or alternatively two contiguous groups $R_7$ with $R_8$ or $R_8$ with $R_9$ or $R_9$ with $R_{10}$ together form a fused benzo group A'; and $R'_7$ with $R'_8$ or $R'_8$ with $R'_9$ or $R'_9$ with $R'_{10}$ together form a fused benzo group B'; with A' and B' optionally substituted with one or more groups chosen from i) nitro; ii) nitroso; iii) $(O)_2S(O^-)$—, $M^+$; iv) hydroxyl; v) mercapto; vi) (di)(alkyl)amino; vii) $R°$—C(X)—X'—; viii) $R°$—X'—C(X)—; ix) $R°$—X'—C(X)—X"—; x) Ar—N═N— and xi) optionally substituted aryl(alkyl)amino; with $M^+$, $R°$, X, X', X" and Ar previously defined; and
W represents a sigma bond 6, an oxygen or sulfur atom, or a divalent radical i) —NR—, with R as defined previously, or ii) methylene —C($R_a$)($R_b$)—, with $R_a$ and $R_b$, which may be identical or different, representing a hydrogen atom or an aryl group, or alternatively $R_a$ and $R_b$ form, with the carbon atom that bears them, a spiro cycloalkyl; preferentially, W represents a sulfur atom or $R_a$ and $R_b$ together form a cyclohexyl;
with the understanding that formulae (II) and (III) comprise at least one sulfonate radical $(O)_2S(O^-)$—, $M^+$ or one carboxylate radical (O)CO⁻—, M⁺ on one of the rings A, A', B, B' or C; preferentially sodium sulfonate.

As non-limiting examples of dyes of formula (II), mention may be made of Acid Red 1, Acid Red 4, Acid Red 13, Acid Red 14, Acid Red 18, Acid Red 27, Acid Red 28, Acid Red 32, Acid Red 33, Acid Red 35, Acid Red 37, Acid Red 40, Acid Red 41, Acid Red 42, Acid Red 44, Pigment red 57, Acid Red 68, Acid Red 73, Acid Red 135, Acid Red 138, Acid Red 184, Food Red 1, Food Red 13, Acid Orange 6, Acid Orange 7, Acid Orange 10, Acid Orange 19, Acid Orange 20, Acid Orange 24, Yellow 6, Acid Yellow 9, Acid Yellow 36, Acid Yellow 199, Food Yellow 3, Acid Violet 3, Acid Violet 7, Acid Violet 14, Acid Blue 113, Acid Blue 117, Acid Black 1, Acid Brown 4, Acid Brown 20, Acid Black 26, Acid Black 52, Food Black 1, Food Black 2 and Food yellow 3 or sunset yellow.

As non-limiting examples of dyes of formula (III), mention may be made of Acid Red 111, Acid Red 134 and Acid yellow 38.

In another exemplary embodiment, the anionic hair dyeing agent may be chosen from the pyrazolone anionic azo dyes of formulae (IV) and (V):

$R_{19}$ and $R_{20}$ together form either a double bond, or a benzo group D', which is optionally substituted;

$R'_{16}$, $R'_{19}$ and $R'_{20}$, which may be identical or different, represent a hydrogen atom or an alkyl or hydroxyl group;

$R_{21}$ represents a hydrogen atom or an alkyl or alkoxy group;

$R_a$ and $R_b$, which may be identical or different, are as defined previously, preferentially $R_a$ represents a hydrogen atom and $R_b$ represents an aryl group;

Y represents either a hydroxyl group or an oxo group;

--------- represents a single bond when Y is an oxo group; and represents a double bond when Y represents a hydroxyl group;

with the understanding that that formulae (IV) and (V) comprise at least one sulfonate radical (O)₂S(O⁻)—, M⁺ or one carboxylate radical C(O)O⁻—, M⁺ on one of the rings D or E; preferentially sodium sulfonate.

As non-limiting examples of dyes of formula (IV), mention may be made of Acid Red 195, Acid Yellow 23, Acid Yellow 27 and Acid Yellow 76.

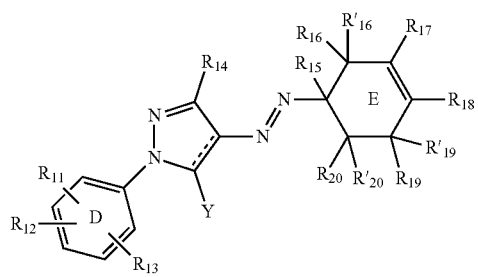

(IV)

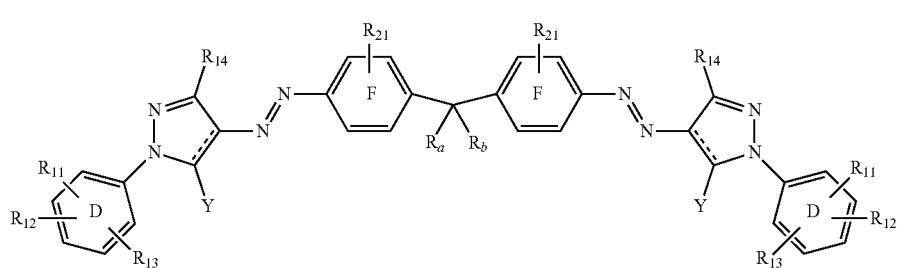

(V)

wherein:
$R_{11}$, $R_{12}$ and $R_{13}$, which may be identical or different, represent a hydrogen or halogen atom, an alkyl group or —(O)₂S(O⁻), M⁺ with M⁺ as defined previously;

$R_{14}$ represents a hydrogen atom, an alkyl group or a group —C(O)O—, M⁺ with M as defined previously;

$R_{15}$ represents a hydrogen atom;

$R_{16}$ represents an oxo group, in which case $R'_{16}$ is absent, or alternatively $R_{15}$ with $R_{16}$ together form a double bond;

$R_{17}$ and $R_{18}$, which may be identical or different, represent a hydrogen atom, or a group chosen from:
(O)₂S(O⁻)—, M⁺ with M⁺ as defined previously;
Ar—O—S(O)₂— with Ar representing an optionally substituted aryl group, preferably a phenyl optionally substituted with one or more alkyl groups;

As a non-limiting example of a dye of formula (V), mention may be made of Acid Yellow 17.

In another exemplary embodiment, the anionic hair dyeing agent may be chosen from the anthraquinone dyes of formulae (VI) and (VII):

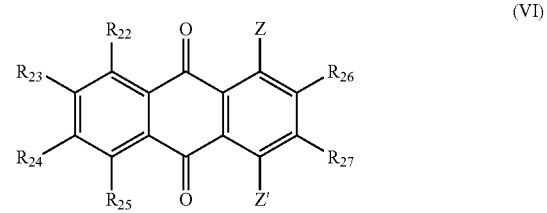

(VI)

-continued

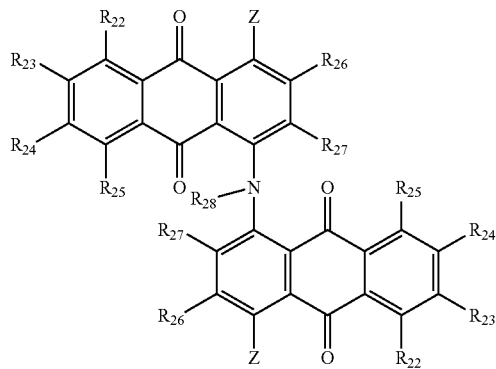
(VII)

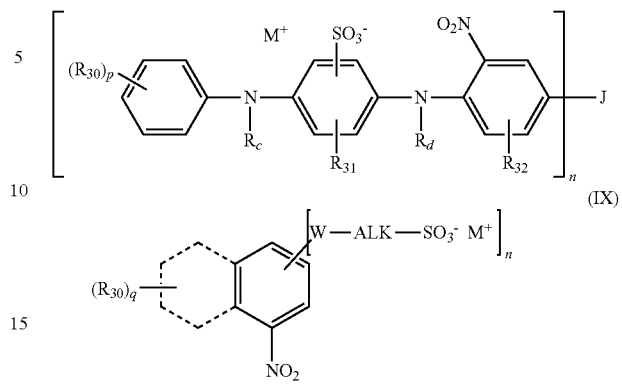
(VIII)

(IX)

wherein:

$R_{22}$, $R_{23}$, $R_{24}$, $R_{25}$, $R_{26}$, and $R_{27}$, which may be identical or different, represent a hydrogen or halogen atom, or a group chosen from:
alkyl;
hydroxyl, mercapto;
alkoxy, alkylthio;
optionally substituted aryloxy or arylthio, preferentially substituted with one or more groups chosen from alkyl and $(O)_2S(O^-)$—, $M^+$ with $M^+$ as defined previously;
aryl(alkyl)amino optionally substituted with one or more groups chosen from alkyl and $(O)_2S(O^-)$—, $M^+$ with $M^+$ as defined previously;
(di)(alkyl)amino;
(di)(hydroxyalkyl)amino;
$(O)_2S(O^-)$—, $M^+$ with $M^+$ as defined previously;

Z' represents a hydrogen atom or a group $NR_{28}R_{29}$ with $R_{28}$ and $R_{29}$, which may be identical or different, representing a hydrogen atom or a group chosen from:
alkyl;
polyhydroxyalkyl such as hydroxyethyl;
aryl optionally substituted with one or more groups, more particularly i) alkyl such as methyl, n-dodecyl, n-butyl; ii) $(O)_2S(O^-)$—, $M^+$ with $M^+$ as defined previously; iii) $R^o$—C(X)—X'—, $R^o$—X'—C(X)—, $R^o$—X'—C(X)—X"— with $R^o$, X, X' and X" as defined previously, preferentially $R^o$ represents an alkyl group;
cycloalkyl; e.g. cyclohexyl;

Z represents a group chosen from hydroxyl and $NR'_{28}R'_{29}$, with $R'_{28}$ and $R'_{29}$, which may be identical or different, representing the same atoms or groups as $R_{28}$ and $R_{29}$ as defined previously;
with the understanding that formulae (VI) and (VII) comprise at least one sulfonate radical $(O)_2S(O^-)$—, $M^+$ or a carboxylate radical $C(O)O$—, $M^+$; preferentially sodium sulfonate.

As non-limiting examples of dyes of formula (VI), mention may be made of Acid Blue 25, Acid Blue 43, Acid Blue 62, Acid Blue 78, Acid Blue 129, Acid Blue 138, Acid Blue 140, Acid Blue 251, Acid Green 25, Acid Green 41, Acid Violet 42, Acid Violet 43, Mordant Red 3, and EXT violet No 2.

As a non-limiting example of a dye of formula (VII), mention may be made of Acid Black 48.

In another exemplary embodiment, the anionic hair dyeing agent may be chosen from the nitro dyes of formulae (VIII) and (IX):

wherein:

$R_{30}$, $R_{31}$ and $R_{32}$, which may be identical or different, represent a hydrogen or halogen atom, or a group chosen from:
alkyl;
alkoxy optionally substituted with one or more hydroxyl groups, alkylthio optionally substituted with one or more hydroxyl groups;
hydroxyl, mercapto;
nitro, nitroso;
polyhaloalkyl;
$R^o$—C(X)—X'—, $R^o$—X'—C(X)—, $R^o$—X'—C(X)—X'— with $R^o$, X, X', and X" as defined previously;
$(O)_2S(O^-)$—, $M^+$ with $M^+$ as defined previously;
$(O)CO^-$—, $M^+$ with $M^+$ as defined previously;
(di)(alkyl)amino;
(di)(hydroxyalkyl)amino;
heterocycloalkyl such as piperidino, piperazino or morpholino;

$R_c$ and $R_d$, which may be identical or different, represent a hydrogen atom or an alkyl group;
W is as defined previously; for example W may represent an —NH— group;
ALK represents a linear or branched divalent $C_1$-$C_6$ alkylene group; more particularly, ALK represents a —$CH_2$—$CH_2$— group;
n is 1 or 2;
p represents an integer inclusively between 1 and 5;
q represents an integer inclusively between 1 and 4;
u is 0 or 1;
when n is 1, J represents a nitro or nitroso group;
when n is 2, J represents an oxygen or sulfur atom, or a divalent radical —$S(O)_m$— with m representing an integer 1 or 2; for example, J represents a radical —$SO_2$—;
M' represents a hydrogen atom or a cationic counterion;

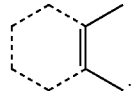

which may be present or absent, represents a benzo group optionally substituted with one or more $R_{30}$ groups as defined previously;

it being understood that formulae (VIII) and (IX) comprise at least one sulfonate radical $(O)_2S(O^-)$—, $M^+$ or a carboxylate radical $C(O)O$—, M; for example sodium sulfonate.

As non-limiting examples of dyes of formula (VIII), mention may be made of Acid Brown 13 and Acid Orange 3.

As non-limiting examples of dyes of formula (IX), mention may be made of Acid Yellow 1, the sodium salt of 2,4-dinitro-1-naphthol-7-sulfonic acid, 2-piperidino-5-nitrobenzenesulfonic acid, 2(4'-N,N(2"-hydroxyethyl)amino-2'-nitro)anilineethanesulfonic acid, 4-p-hydroxyethylamino-3-nitrobenzenesulfonic acid, and EXT D&C yellow 7.

In another exemplary embodiment, the anionic hair dyeing agent may be chosen from the triarylmethane dyes of formula (X):

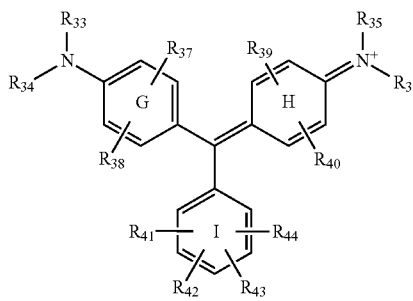

wherein:
$R_{33}$, $R_{34}$, $R_{35}$ and $R_{36}$, which may be identical or different, represent a hydrogen atom or a group chosen from alkyl, optionally substituted aryl and optionally substituted arylalkyl; particularly an alkyl and benzyl group optionally substituted with a group $(O)_mS(O^-)$—, M with $M^+$ and m as defined previously;
$R_{37}$, $R_{38}$, $R_{39}$, $R_{40}$, $R_{41}$, $R_{42}$, $R_{43}$ and $R_{44}$, which may be identical or different, represent a hydrogen atom or group chosen from:
alkyl;
alkoxy, alkylthio;
(di)(alkyl)amino;
hydroxyl, mercapto;
nitro, nitroso;
$R°$—C(X)—X'—, $R°$—X'—C(X)—, $R°$—X'—C(X)—X"— with $R°$ representing a hydrogen atom or an alkyl or aryl group; X, X' and X", which may be identical or different, representing an oxygen or sulfur atom, or NR with R representing a hydrogen atom or an alkyl group;
$(O)_2S(O^-)$—, $M^+$ with $M^+$ representing a hydrogen atom or a cationic counterion;
$(O)CO^-$—, $M^+$ with $M^+$ as defined previously;
or alternatively two contiguous groups $R_{41}$ with $R_{42}$ or $R_{42}$ with $R_{43}$ or $R_{43}$ with $R_{44}$ together form a fused benzo group: I'; with I' optionally substituted with one or more groups chosen from i) nitro; ii) nitroso; iii) $(O)_2S(O^-)$—, $M^+$; iv) hydroxyl; v) mercapto; vi) (di)(alkyl)amino; vii) $R°$—C(X)—X'—; viii) $R°$—X'—C(X)—; ix) $R°$—X'—C(X)—X"—; with $M^+$, $R°$, X, X' and X" as defined previously;
with the understanding that at least one of the rings G, H, I or I' comprises at least one sulfonate radical $(O)_2S(O^-)$— or a carboxylate radical —C(O)O—; for example sulfonate.

In a preferred embodiment of formula (X), $R_{37}$ to $R_{40}$ represent a hydrogen atom, and $R_{41}$ to $R_{44}$ which may be identical or different, represent a hydroxyl group or $(O)_2S$ $(O^-)$—, $M^+$; and when $R_{43}$ with $R_{44}$ together form a benzo group, it is preferentially substituted with an $(O)_2S(O^-)$— group.

As non-limiting examples of dyes of formula (X), mention may be made of Acid Blue 1; Acid Blue 3; Acid Blue 7, Acid Blue 9; Acid Violet 49; Acid Green 3; Acid Green 5 and Acid Green 50.

In another exemplary embodiment, the anionic hair dyeing agent may be chosen from the xanthene-based dyes of formula (XI):

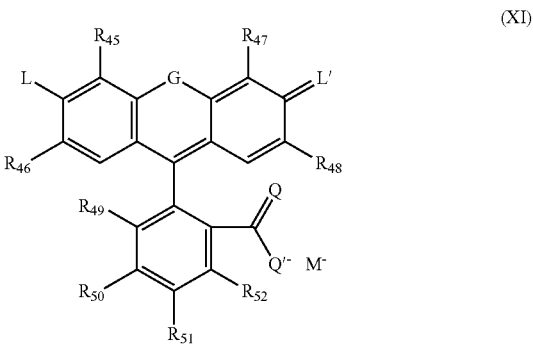

wherein:
$R_{45}$, $R_{46}$, $R_{47}$ and $R_{48}$, which may be identical or different, represent a hydrogen or halogen atom;
$R_{49}$, $R_{50}$, $R_{51}$ and $R_{52}$, which may be identical or different, represent a hydrogen or halogen atom, or a group chosen from:
alkyl;
alkoxy, alkylthio;
hydroxyl, mercapto;
nitro, nitroso;
$(O)_2S(O^-)$—, $M^+$ with $M^+$ representing a hydrogen atom or a cationic counterion;
$(O)CO^-$—, $M^+$ with $M^+$ as defined previously;
G represents an oxygen or sulfur atom or a group $NR_e$ with $R_e$ as defined previously;
L represents an alkoxide $O^-$, $M^+$; a thioalkoxide $S^-$, $M^+$ or a group $NR_f$ with $R_f$ representing a hydrogen atom or an alkyl group and $M^+$ as defined previously; $M^+$ is particularly sodium or potassium;
L' represents an oxygen or sulfur atom or an ammonium group: $N^+R_fR_g$, with $R_f$ and $R_g$, which may be identical or different, representing a hydrogen atom, an alkyl group or optionally substituted aryl; for example L' represents an oxygen atom or a phenylamino group optionally substituted with one or more alkyl or $(O)_mS$ $(O^-)$—, $M^+$ groups with m and $M^+$ as defined previously;
Q and Q', which may be identical or different, represent an oxygen or sulfur atom; and
$M^+$ is as defined previously.

As non-limiting examples of dyes of formula (XI), mention may be made of Acid Yellow 73; Acid Red 51; Acid Red 52; Acid Red 87; Acid Red 92; Acid Red 95 and Acid Violet 9.

In another exemplary embodiment, the anionic hair dyeing agent may be chosen from the indole-based dyes of formula (XII):

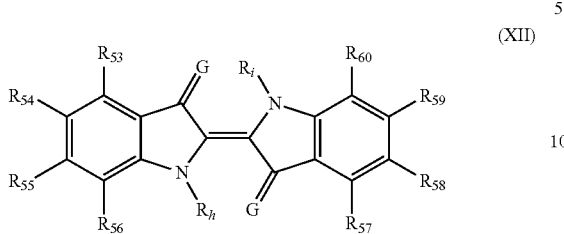

(XII)

wherein:

$R_{53}$, $R_{54}$, $R_{55}$, $R_{56}$, $R_{57}$, $R_{58}$, $R_{59}$ and $R_{60}$, which may be identical or different, represent a hydrogen atom or group chosen from:
alkyl;
alkoxy, alkylthio;
hydroxyl, mercapto;
nitro, nitroso;
$R^o$—C(X)—X'—, $R^o$—X'—C(X)—, $R^o$—X'—C(X)—X"— with $R^o$ representing a hydrogen atom or an alkyl or aryl group; X, X' and X", which may be identical or different, representing an oxygen or sulfur atom, or NR with R representing a hydrogen atom or an alkyl group;
$(O)_2S(O^-)$—, $M^+$ with $M^+$ representing a hydrogen atom or a cationic counterion;
$(O)CO^-$—, $M^+$ with $M^+$ as defined previously;
G represents an oxygen or sulfur atom or a group $NR_e$ with $R_e$ as defined previously;
$R_1$ and Rh, which may be identical or different, represent a hydrogen atom or an alkyl group;
it being understood that formula (XII) comprises at least one sulfonate radical $(O)_2S(O^-)$—, $M^+$ or a carboxylate radical —C(O)O—, $M^+$; for example sodium sulfonate.

As a non-limiting example of a dye of formula (XII), mention may be made of Acid Blue 74.

In another exemplary embodiment, the anionic hair dyeing agent may be chosen from the quinoline-based dyes of formula (XIII):

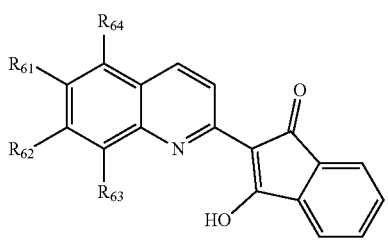

(XIII)

wherein:

$R_{61}$ represents a hydrogen or halogen atom or an alkyl group;
$R_{62}$, $R_{63}$, and $R_{64}$, which may be identical or different, represent a hydrogen atom or a group $(O)_2S(O^-)$—, $M^+$ with $M^+$ representing a hydrogen atom or a cationic counterion;
or alternatively $R_{61}$ with $R_{62}$, or $R_{61}$ with $R_{64}$, together form a benzo group optionally substituted with one or more groups $(O)_2S(O^-)$—, $M^+$ with $M^+$ representing a hydrogen atom or a cationic counterion;
it being understood that formula (XIII) comprises at least one sulfonate radical $(O)_2S(O^-)$—, for example sodium sulfonate.

As non-limiting examples of dyes of formula (XIII), mention may be made of Acid Yellow 2, Acid Yellow 3 and Acid Yellow 5.

Without limitation, exemplary anionic hair dyeing agents may be chosen from (C.I. 45380) Acid Red 87 (formula XI); (C.I. 10316) Sodium salt of 2,4-dinitro-1-naphthol-7-sulfonic acid (formula IX); (C.I. 10383) Acid Orange 3 (formula VIII); (C.I. 13015) Acid Yellow 9/Food Yellow 2 (formula II); (C.I. 14780) Direct Red 45/Food Red 13 (formula II); (C.I. 13711) Acid Black 52 (formula II); (C.I. 13065) Acid Yellow 36 (formula II); (C.I. 14700) Sodium salt of 1-hydroxy-2-(2',4'-xylyl-5-sulfonatoazo)naphthalene-4-sulfonic acid/Food Red 1 (formula II); (C.I. 14720) Acid Red 14/Food Red 3/Mordant Blue 79 (formula II); (C.I. 14805) Sodium salt of 4-hydroxy-3-[(2-methoxy-5-nitrophenyl)diaza]-6-(phenylamino)naphthalene-2-sulfonic acid/Acid Brown 4 (formula II); (C.I. 15510) Acid Orange 7/Pigment Orange 17/Solvent Orange 4 (formula II); (C.I. 15985) Food Yellow 3/Pigment Yellow 104 (formula II); (C.I. 16185) Acid Red 27/Food Red 9 (formula II); (C.I. 16230) Acid Orange 10/Food Orange 4 (formula II); (C.I. 16250) Acid Red 44 (formula II); (C.I. 17200) Acid Red 33/Food Red 12 (formula II); (C.I. 15685) Acid Red 184 (formula II); (C.I. 19125) Acid Violet 3 (formula II); (C.I. 18055) Sodium salt of 1-hydroxy-2-(4'-acetamidophenylazo)-8-acetamidonaphthalene-3,6-disulfonic acid/Acid Violet 7/Food Red 11 (formula II); (C.I. 18130) Acid Red 135 (formula II); (C.I. 19130) Acid Yellow 27 (formula IV); (C.I. 19140) Acid Yellow 23/Food Yellow 4 (formula IV); (C.I. 20170) 4'-(sulfonato-2",4"-dimethyl)bis(2,6-phenylazo)-1,3-dihydroxybenzene/Acid Orange 24 (formula II); (C.I. 20470) Sodium salt of 1-amino-2-(4'-nitrophenylazo)-7-phenylazo-8-hydroxy-naphthalene-3,6-disulfonic acid/Acid Black 1 (formula II); (C.I. 23266) (4-((4-methylphenyl)sulfonyloxy) phenylazo)-2,2'-dimethyl-4-((2-hydroxy-5,8-disulfonato) naphthylazo)biphenyl/Acid Red 111 (formula III); (C.I. 27755) Food Black 2 (formula II) (C.I. 25440) 1-(4'-sulfonatophenylazo)-4-((2"-hydroxy-3"-acetylamino-6",8"-disulfonato)naphthylazo)-6-sulfonatonaphthalene (tetrasodium salt)/Food Black 1 (formula II), (C.I. 42090) Acid Blue 9 (formula X) (C.I. 60730) Acid Violet 43 (formula VI) (C.I. 61570) Acid Green 25 (formula VI), (C.I. 62045) Sodium salt of 1-amino-4-cyclohexylamino-9,10-anthraquinone-2-sulfonic acid/Acid Blue 62 (formula VI), (C.I. 62105) Acid Blue 78 (formula VI), (C.I. 14710) Sodium salt of 4-hydroxy-3-((2-methoxyphenyl)azo)-1-naphthalenesulfonic acid/Acid Red 4 (formula II); 2-Piperidino-5-nitrobenzenesulfonic acid (formula IX); 2-(4'-N,N-(2"-Hydroxyethyl) amino-2'-nitro)anilineethanesulfonic acid (formula IX); 4-β-Hydroxyethylamino-3-nitrobenzenesulfonic acid (formula IX); (C.I. 42640) Acid Violet 49 (formula X); (C.I. 42080) Acid Blue 7 (formula X); (C.I. 58005) Sodium salt of 1,2-dihydroxy-3-sulfoanthraquinone/Mordant Red 3 (formula VI); (C.I. 62055) Sodium salt of 1-amino-9,10-dihydro-9,10-dioxo-4-(phenylamino) 2-anthracenesulfonic acid/Acid Blue 25 (formula VI); or (C.I. 14710) Sodium salt of 4-hydroxy-3-((2-methoxyphenyl)azo)-1-naphthalenesulfonic acid/Acid Red 4 (formula II).

By way of example, neutral hair dyeing agents may be chosen from HC Blue 2, HC Blue 4, HC Blue 5, HC Blue 6, HC Blue 7, HC Blue 8, HC Blue 9, HC Blue 10, HC Blue 11, HC Blue 12, HC Blue 13, HC Brown 1, HC Brown 2, HC Green 1, HC Orange 1, HC Orange 2, HC Orange 3, HC Orange 5, HC Red BN, HC Red 1, HC Red 3, HC Red 7, HC Red 8, HC Red 9, HC Red 10, HC Red 11, HC Red 13, HC Red 54, HC Red 14, HC Violet BS, HC Violet 1, HC Violet 2, HC Yellow 2, HC Yellow 4, HC Yellow 5, HC Yellow 6, HC Yellow 7, HC Yellow 8, HC Yellow 9, HC Yellow 10, HC Yellow 11, HC Yellow 12, HC Yellow 13, HC Yellow 14, HC Yellow 15, 2-amino-6-chloro-4-nitrophenol, picramic acid, 1,2-diamino-4-nitrobenzene, 1,4-diamino-2-nitrobenzene, 3-nitro-4-aminophenol, 1-hydroxy-2-amino-3-nitrobenzene, 2-hydroxyethyl picramic acid, 3-nitro-p-hydroxyethylaminophenol, and 4-hydroxypropylamino-3-nitrophenol N,N-bis(2-hydroxyethyl)-2'-nitro-p-phenylenediamine.

Natural acidic or neutral hair dyeing agents may also be chosen. As used herein, the term "natural" hair dyeing agents include dyes derived from natural materials (plant, mineral or animal origin), for instance extracts, ground material and decoctions, which have a greater or smaller concentration of dyes. Without being limiting, exemplary natural hair dyeing agents may be chosen from spinulosin, orceins, curcumin, indole derivatives such as isatin or indole-2,3-dione, indigoids including indigo, phthalocyanines, and porphyrins optionally complexed to a metal, glycosyl or non-glycosyl iridoids, chromene dyes, anthraquinone and naphthoquinone dyes such as lawsone or henna, juglone, spinulosin, chromene or chroman dyes, such as neoflavanols and neoflavanones, flavanols, and anthocyanidols. Use may also be made of extracts containing these natural dyes, for example plant extracts or poultices containing said dyes.

In various exemplary embodiments, the microtubes may be loaded with an amount of hair dyeing agent ranging from about 0.01% to about 30% by weight, based on the weight of the microtube prior to loading, such as about 0.1% to about 15%, about 0.1% to about 10%, about 0.1% to about 9%, about 0.1% to about 8%, about 0.1% to about 7%, about 0.1% to about 6%, about 0.1% to about 5%, about 0.1% to about 4%, about 0.1% to about 3%, about 0.1% to about 2%, about 0.1% to about 1%, about 0.5% to about 10%, about 0.5% to about 9%, about 0.5% to about 8%, about 0.5% to about 7%, about 0.5% to about 6%, about 0.5% to about 5%, about 0.5% to about 4%, about 0.5% to about 3%, about 0.5% to about 2%, about 0.5% to about 1%, about 1% to about 10%, about 1% to about 9%, about 1% to about 8%, about 1% to about 7%, about 1% to about 6%, about 1% to about 5%, about 1% to about 4%, about 1% to about 3%, or about 1% to about 2% by weight, based on the weight of the microtube prior to loading, including all subranges thereof.

The dyeing composition optionally comprises a solvent, in which the microtube-dye composite may be dispersed. The solvent may be chosen from water, non-aqueous solvents, or a mixture thereof. The solvent will advantageously be chosen so that it will not interfere with deposition of the microtube-dye composite on the hair, and that it will not damage or irritate the hair, scalp, and/or skin. In various embodiments, the solvent comprises, consists essentially of, or consists of water.

Exemplary non-aqueous solvents include, for example, glycerin, $C_{1-4}$ alcohols, organic solvents, fatty alcohols, fatty ethers, fatty esters, polyols, glycols, vegetable oils, mineral oils, liposomes, laminar lipid materials, and mixtures thereof. As examples of organic solvents, non-limiting mentions can be made of monoalcohols and polyols such as ethyl alcohol, isopropyl alcohol, propyl alcohol, benzyl alcohol, and phenylethyl alcohol, or glycols or glycol ethers such as, for example, monomethyl, monoethyl and monobutyl ethers of ethylene glycol, propylene glycol or ethers thereof such as, for example, monomethyl ether of propylene glycol, butylene glycol, hexylene glycol, dipropylene glycol as well as alkyl ethers of diethylene glycol, for example monoethyl ether or monobutyl ether of diethylene glycol. The organic solvents can be volatile or non-volatile compounds.

Further non-limiting examples of solvents which may be used include alkanediols (polyhydric alcohols) such as glycerin, 1,2,6-hexanetriol, trimethylolpropane, ethylene glycol, propylene glycol, diethylene glycol, triethylene glycol, tetraethylene glycol, pentaethylene glycol, dipropylene glycol, 2-butene-1,4-diol, 2-ethyl-1,3-hexanediol, 2-methyl-2,4-pentanediol, caprylyl glycol, 1,2-hexanediol, 1,2-pentanediol, and 4-methyl-1,2-pentanediol; alkyl alcohols having 1 to 4 carbon atoms such as ethanol, methanol, butanol, propanol, and isopropanol; glycol ethers such as ethylene glycol monomethyl ether, ethylene glycol monoethyl ether, ethylene glycol monobutyl ether, ethylene glycol monomethyl ether acetate, diethylene glycol monomethyl ether, diethylene glycol monoethyl ether, diethylene glycol mono-n-propyl ether, ethylene glycol mono-iso-propyl ether, diethylene glycol mono-iso-propyl ether, ethylene glycol mono-n-butyl ether, ethylene glycol mono-t-butyl ether, diethylene glycol mono-t-butyl ether, 1-methyl-1-methoxybutanol, propylene glycol monomethyl ether, propylene glycol monoethyl ether, propylene glycol mono-t-butyl ether, propylene glycol mono-n-propyl ether, propylene glycol mono-iso-propyl ether, dipropylene glycol monomethyl ether, dipropylene glycol monoethyl ether, dipropylene glycol mono-n-propyl ether, and dipropylene glycol mono-iso-propyl ether; 2-pyrrolidone, N-methyl-2-pyrrolidone, 1,3-dimethyl-2-imidazolidinone, formamide, acetamide, dimethyl sulfoxide, sorbit, sorbitan, acetine, diacetine, triacetine, sulfolane, and mixtures thereof.

The solvent may be present in the dyeing composition in an amount ranging from about 50% to about 99.9% by weight, relative to the total weight of the dyeing composition. For example, the total amount of solvent may range from about 80% to about 99%, about 80% to about 98%, about 80% to about 97%, about 80% to about 96%, about 80% to about 95%, about 80% to about 94%, about 80% to about 93%, about 80% to about 92%, about 80% to about 91%, or about 80% to 90% by weight, relative to the total weight of the dyeing composition.

The dyeing composition may comprise additional components, as long as such additional components do not substantially interfere with the deposition of the microtube-dye composite onto the hair. By way of example only, the dyeing composition may comprise pH adjusters, preservatives, humectants, oils, fragrances, etc.

In various embodiments, the dyeing composition has a pH of less than or equal to 7.

The microtube-dye composite may be present in the dyeing composition in an amount ranging from about 0.01% to about 15% by weight, based on the weight of the dyeing composition, such as about 0.1% to about 10%, about 0.1% to about 9%, about 0.1% to about 8%, about 0.1% to about 7%, about 0.1% to about 6%, about 0.1% to about 5%, about 0.1% to about 4%, about 0.1% to about 3%, about 0.1% to about 2%, about 0.1% to about 1%, about 0.5% to about 10%, about 0.5% to about 9%, about 0.5% to about 8%, about 0.5% to about 7%, about 0.5% to about 6%, about 0.5% to about 5%, about 0.5% to about 4%, about 0.5% to about 3%, about 0.5% to about 2%, about 0.5% to about 1%, about 1% to about 10%, about 1% to about 9%, about 1% to about 8%, about 1% to about 7%, about 1% to about 6%, about 1% to about 5%, about 1% to about 4%, about 1% to about 3%, or about 1% to about 2% by weight, based on the weight of the dyeing composition, including all subranges thereof.

It should be understood that the microtube-dye composite included in the dyeing composition can include mixtures of different microtubes, mixtures of different dyes, or both. By way of example only, a first set of microtubes comprising halloysite may be loaded with one dye, a second set of microtubes comprising halloysite may be loaded with a second dye, and the first and second sets of microtube-dye composites may be included in the dyeing composition. As a further example, a first set of microtubes comprising halloysite may be loaded with one dye, a second set of microtubes comprising a structure other than halloysite may be loaded with a second dye, and the first and second sets of microtube-dye composites may be included in the dyeing composition.

Methods

It has been discovered that altering the color of the hair using systems according to the disclosure has the surprising and unexpected benefit of imparting improved color deposition and vibrancy. In particular, while it was previously discovered that microtube-dye composites can be used to impart color to hair, the previous methods experienced the drawbacks of limited deposition of color and limited vibrancy, particularly on hair that was natural, not previously treated, and/or not damaged.

Exemplary methods according to the disclosure include treating the hair with the pretreatment composition, optionally removing the pretreatment composition from the hair, and treating the hair with the dyeing composition.

In methods according to the disclosure, the hair is first treated with the pretreatment composition, which may, for example, be an aqueous composition comprising at least one cationic surfactant in an amount ranging from about 0.1% to about 10%, by applying the pretreatment composition to the hair and optionally massaging or combing the composition throughout the hair to ensure complete coverage. The pretreatment composition may be applied to the hair in an amount ranging up to about 5 grams per gram of hair, for example about 4 grams per gram of hair, about 3 grams per gram of hair, about 2 grams per gram of hair, or about 1 gram per gram of hair.

The pretreatment composition may, for example, be left on the hair for a period of time ranging up to about 20 minutes, such as, for example, about 30 seconds to about 10 minutes, about 1 minute to about 5 minutes, about 1 minute to about 3 minutes, or about 3 minutes to about 5 minutes. The pretreatment composition is preferably completely or substantially completely removed from the hair after the leave-on period. The pretreatment composition can be removed in any manner, such as, for example, by rinsing the hair with water or by using a towel to remove the composition from the hair.

The methods include a step of applying the dyeing composition to the hair after the pretreatment composition is applied to, and optionally removed from, the hair. The dyeing composition may, for example, be an aqueous composition comprising at least one microtube-dye composite in an amount ranging from about 0.1% to about 10%, which may optionally be massaged or combed throughout the hair to ensure complete coverage. The dyeing composition may be applied to the hair in an amount ranging up to about 5 grams per gram of hair, for example about 4 grams per gram of hair, about 3 grams per gram of hair, about 2 grams per gram of hair, or about 1 gram per gram of hair.

The dyeing composition may be left on the hair for a leave-in period of time sufficient to achieve the desired coloration effect. For example, the dyeing composition may be left on the hair for up to one hour, such as from about 3 minutes to about 45 minutes, from about 5 minutes to about 40 minutes, from about 10 minutes to about 35 minutes, or from about 15 minutes to about 30 minutes. One skilled in the art will be able to determine an appropriate amount of time to leave the hair color composition or the mixture on the hair in order to achieve the desired effect.

While the dyeing composition is on the hair, the microtube-dye composite may self-assemble in and around hair cuticles, attaching to the hair fiber and providing a layer of the composite on the fiber of up to a few micrometers, which imparts color to the hair. For example, the layer of the composite on the hair fiber may range up to about 5 µm, such as up to about 4 µm, up to about 3 µm, up to about 2 µm, or up to about 1 µm. The layer may range from about 1µ to about 5 µm, such as about 1µ to about 4 µm, about 1µ to about 3 µm, about 1µ to about 2 µm, about 2µ to about 5 µm, about 2µ to about 4 µm, about 2µ to about 3 µm, about 3µ to about 5 µm, or about 4µ to about 5 µm. In various embodiments, this self-assembly process provides the additional benefit of being less damaging to the hair than traditional hair color altering processes. For example, harsh alkaline conditions are not typically required in order to achieve satisfying vibrant colors according to methods of the disclosure.

The dyeing composition may be rinsed from the hair, and the hair may optionally be washed, rinsed, dried, and/or styled in any conventional manner.

Kits

In a further embodiment, the disclosure relates to kits comprising the systems described herein. According to various embodiments, the kits may be multi-compartment or multi-container kits, where the compartments or containers are mutually separate. For example, the kits may comprise at least two compartments or containers, with a first compartment or container containing a pretreatment composition, and a second compartment or container containing a dyeing composition according to the disclosure. In further embodiments, the kits may comprise at least three, at least four, or more compartments or containers.

The compartments or containers of kits according to the disclosure can be in any configuration, without limitation. For example, they can be a bottle, a tube, a sachet, an ampoule, or any other container configured to contain the additive composition or shampoo composition mutually separately in the kit. Kits may optionally include additional compartments for additional components.

Various exemplary embodiments of kits according to the disclosure comprise:

a first compartment or container containing a pretreatment composition comprising:

at least one cationic surfactant; and at least one solvent; and a second compartment or container containing a dyeing composition comprising:

at least one microtube-dye composite, wherein, in the microtube-dye composite, the dye comprises at least one anionic or neutral hair dyeing agent; and at least one solvent.

Further exemplary embodiments of kits according to the disclosure comprise:
- a first compartment or container containing a pretreatment composition comprising:
  - at least one cationic surfactant chosen from compounds of formula (I); and
  - at least one solvent comprising water; and
- a second compartment or container containing a dyeing composition comprising:
  - at least one halloysite-dye composite, wherein, in the halloysite-dye composite, the dye comprises at least one anionic or neutral hair dyeing agent; and
  - at least one solvent comprising water.

In yet further exemplary embodiments, kits according to the disclosure comprise:
- a first compartment or container containing a pretreatment composition comprising:
  - from about 0.001% to about 25% of at least one cationic surfactant chosen from quaternary ammonium salts of formula (I):

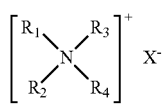

wherein $R_1$ to $R_4$, which may be identical or different, are chosen from a linear or branched aliphatic group comprising from 1 to 30 carbon atoms or an aromatic group, wherein at least one of the groups $R_1$ to $R_4$ comprise from 12 to 22 carbon atoms, and $X^-$ is an anionic counterion chosen from halides; and
water; and
- a second compartment or container containing a dyeing composition comprising:
  - from about 0.01% to about 15% of at least one halloysite-dye composite, wherein, in the halloysite-dye composite, the dye comprises at least one anionic or neutral hair dyeing agent; and
  - water.

It is to be understood that, in exemplary kits according to the disclosure, the pretreatment composition(s) and dyeing composition(s) can be as described herein for various systems, methods, and examples, for example with regard to particular components and/or ranges thereof.

Various alternate exemplary embodiments of kits according to the disclosure comprise:
- a first compartment or container containing a pretreatment composition comprising at least one cationic surfactant; and
- a second compartment or container containing a dyeing composition comprising at least one microtube-dye composite, wherein, in the microtube-dye composite, the dye comprises at least one anionic or neutral hair dyeing agent.

Thus, in some embodiments, the pretreatment and/or dyeing composition may not be present in the kit in a solvent, or may be present in the kit in a solvent but in concentrated form. For example, the pretreatment and/or dyeing composition may be present in the kit in solid or powder form, and the user may mix the solid or powder with a solvent, such as water, prior to use. Alternatively, the pretreatment and/or dyeing composition may be present in the form of a gel or thickened liquid that is to be mixed with a solvent, such as water, prior to use. In such embodiments, a kit with more than two compartments or containers may be envisioned. For example, a kit with three (and/or four) compartments or containers, where a third (and/or fourth) compartment or container includes a solvent, e.g. to mix with the pretreatment composition and/or dyeing composition, may be chosen.

Kits may also include additional components or compartments, such as, for example, instructions or an apparatus or tool for applying the pretreatment and/or dyeing compositions onto the hair, e.g. an applicator brush, and/or a compartment for the same.

As used herein, the terms "comprising," "having," and "including" (or "comprise," "have," and "include") are used in their open, non-limiting sense.

The terms "a," "an," and "the" are understood to encompass the plural as well as the singular.

As used herein, the phrases "and mixtures thereof," "and a mixture thereof," "and combinations thereof," "and a combination thereof," "or mixtures thereof," "or a mixture thereof," "or combinations thereof," and "or a combination thereof," are used interchangeably to denote that the listing of components immediately preceding the phrase, such as "A, B, C, D, or mixtures thereof" signify that the component(s) may be chosen from A, from B, from C, from D, from A+B, from A+B+C, from A+D, from A+C+D, etc., without limitation on the variations thereof. Thus, the components may be used individually or in any combination thereof.

Other than in the operating examples, or where otherwise indicated, all numbers expressing quantities of ingredients and/or reaction conditions are to be understood as being modified in all instances by the term "about," meaning within +/−5% of the indicated number.

All percentages, parts and ratios herein are based upon the total weight of the compositions of the present invention, unless otherwise indicated.

As used herein, all ranges provided are meant to include every specific range within, and combination of sub ranges between, the given ranges. Thus, a range from 1-5, includes specifically 1, 2, 3, 4, and 5, as well as sub ranges such as 2-5, 3-5, 2-3, 2-4, 1-4, etc. All ranges and values disclosed herein are inclusive and combinable. For examples, any value or point described herein that falls within a range described herein can serve as a minimum or maximum value to derive a sub-range, etc.

The term "substantially free" or "essentially free" as used herein means that there is less than about 5% by weight of a specific material added to a composition, based on the total weight of the compositions. Nonetheless, the compositions may include less than about 3%, less than about 2%, less than about 1%, less than about 0.5%, less than about 0.1%, or less than about 0.01% of the specified material.

It is to be understood that the use of the terms "treat," "treated," "treatment," and variations thereof is not intended to be limiting, but rather is merely intended to indicate that one or more compositions is applied to the hair, and optionally removed from the hair, as described herein. For example, hair that is "treated" with a pretreatment composition according to the disclosure may have had the pretreatment composition applied, and/or may have had the pretreatment composition applied and removed, e.g. by rinsing or towel drying. As a further example, hair that is "treated" with a dyeing composition according to the disclosure may have had the dyeing composition applied, and/or may have had the dyeing composition applied and rinsed from the hair. As yet a further example, hair that is "treated" with a system according to the disclosure may have had the pretreatment composition applied and optionally removed, and additionally may have had the dyeing composition applied and optionally rinsed from the hair.

All publications and patent applications cited in this specification are herein incorporated by reference, and for any and all purposes, as if each individual publication or patent application were specifically and individually indicated to be incorporated by reference. In the event of an inconsistency between the present disclosure and any publications or patent application incorporated herein by reference, the present disclosure controls.

The examples that follow serve to illustrate embodiments of the present disclosure without, however, being limiting in nature. It will be apparent to those skilled in the art that various modifications and variations can be made in the delivery system, compositions, and methods of the invention without departing from the spirit or scope of the invention.

EXAMPLES

Implementation of various non-limiting embodiments of the disclosure is demonstrated by way of the following Examples.

In the Examples, the change in the color of hair is evaluated with the L* a* b* system, using Colorshot MS. The change in color (ΔE) is defined as:

$$\Delta E_{ab}^* = \sqrt{(L_2^* - L_1^*)^2 + (a_2^* - a_1^*)^2 + (b_2^* - b_1^*)^2}$$

The greater the value for ΔE, the greater the difference in color relative to the hair prior to treatment.

Example 1A—Microtube-Dye Composites

Three separate halloysite-dye composites were prepared with 5-12 wt % dyes loaded, relative to the weight of the halloysite nanotube prior to loading, according to the following procedure.

The dye (Acid Blue 9, Acid Red 40, or Acid Black) was dissolved in 75% ethanol/25% water. Unmodified halloysite was added and stirred. The dispersion was subjected to three vacuum cycles of 30 minutes each. The halloysite-dye composites were washed and dried.

Example 1B—Microtube-Dye Composites

Three separate halloysite-dye composites were prepared according to the following procedure.

The dye (Acid Black 1, Acid Red 33, or Curcumin) was dissolved in deionized water. Unmodified halloysite was added and stirred. The dispersion was then sonicated for 5 minutes, mixed for 30 minutes under ambient pressure, then mixed under vacuum (0.15 atm) for another 30 minutes. The mixing step was repeated 3 times, after which the slurry was centrifuged to remove the supernatant and the composite was washed with solvent and dried in oven at 50° C. The dried composite was ground into a fine powder, to provide halloysite-dye composites having the following dye loading.

| Halloysite-Dye Composite | Dye Loading |
|---|---|
| Halloysite-Acid Red 33 | 5.6% |
| Halloysite-Acid Black 1 | 3.9% |
| Halloysite-Curcumin | 1.3% |

Example 2—Pretreatment Compositions

Four separate inventive pretreatment compositions were prepared by dissolving behentrimonium chloride, cetrimonium chloride, dodecyltrimethylammonium chloride, or dodecyltrimethylammonium bromide in water, with heating, as needed, to prepare a 5 wt % aqueous solution. One comparative pretreatment composition was prepared according to the same method, using a non-ionic surfactant, Triton X-100 (2-[4-(2,4,4-trimethylpentan-2-yl)phenoxy]ethanol).

| | Surfactant | Pretreatment Composition |
|---|---|---|
| Inventive (Cationic) | behentrimonium chloride | BTAC |
| | cetrimonium chloride | CTAC |
| | dodecyltrimethylammonium chloride | DTAC |
| | dodecyltrimethylammonium bromide | DTAB |
| Comparative (Non-ionic) | Triton X-100 | Triton X-100 |

Example 3A—Dyeing Compositions

Three separate dyeing compositions were prepared using the halloysite-dye composites prepared in Example 1B, by mixing each of the composites with water to prepare a 5 wt % aqueous solution.

| Halloysite-Dye Composite | Dyeing Composition |
|---|---|
| Halloysite-Acid Red 33 | HNT-AR33 (5.0%) |
| Halloysite-Acid Black 1 | HNT-AB1 (5.0%) |
| Halloysite-Curcumin | HNT-CCM (5.0%) |

Example 3B—Dyeing Composition

A dyeing composition was prepared using the Halloysite-Acid Red 33 composite prepared in Example 1B, by mixing the composite with water to prepare a 0.28 wt % aqueous solution.

| Halloysite-Dye Composite | Dyeing Composition |
|---|---|
| Halloysite-Acid Red 33 | HNT-AR33 (0.28%) |

Example 3C—Dyeing Composition

Two dyeing compositions were prepared using the Halloysite-Curcumin composite prepared in Example 1B, by mixing an amount of the composite with water to prepare either a 0.5 wt % aqueous solution or a 5 wt % aqueous solution.

| Halloysite-Dye Composite | Dyeing Composition |
|---|---|
| Halloysite-Curcumin | HNT-CCM (0.5%) |
| Halloysite-Curcumin | HNT-CCM (5%) |

Example 4—Methods of Altering the Color of Hair

The following combinations of pretreatment compositions according to Example 2 and dyeing compositions according to Example 3A were applied to swatches of hair:

| Example | | Pretreatment Composition | Dyeing Composition |
|---|---|---|---|
| Inventive | 4A | BTAC | HNT-AR33 (5.0%) |
| | 4B | CTAC | HNT-AR33 (5.0%) |
| | 4C | DTAC | HNT-AR33 (5.0%) |
| Comparative | 4D | Triton X-100 | HNT-AR33 (5.0%) |
| | 4E | None | HNT-AR33 (5.0%) |

The process for Examples 4A-4D was as follows. First, the pretreatment composition was applied to swatches of 90% grey virgin hair at a ratio of 2 grams per 1 gram of hair and massaged through the hair to ensure maximum coverage. After a leave-in period of approximately 3 minutes, the pretreatment composition was rinsed from the hair with 10 passes of tap water. The excess water was squeezed from the hair. Subsequently, the dyeing composition was applied to the hair at a ratio of 2 grams per 1 gram of hair and massaged through the hair to ensure maximum coverage. After a leave-in period of approximately 30 minutes, the hair was rinsed with 10 passes of tap water (~37° C.). The hair was then dried, and the color change was evaluated.

For Example 4E (no pretreatment), the dyeing composition was applied to the hair at a ratio of 2 grams per 1 gram of hair and massaged through the hair to ensure maximum coverage. After a leave-in period of approximately 30 minutes, the hair was rinsed with 10 passes of tap water (~37° C.). The hair was then dried, and the color change was evaluated.

As seen in FIG. 1, the hair of inventive Examples 4A-4C shows the greatest change in ΔE (greatest color change) compared to the hair prior to treatment, with Example 4B, having pretreated the hair with a composition comprising cetyltrimethylammonium chloride followed by dyeing the hair with the halloysite-dye composite, surprisingly showed the greatest enhancement in color deposition and vibrancy. The hair of comparative Example 4D, following the same method but using a pretreatment composition not according to the disclosure, and the hair of comparative Example 4E, with no pretreatment step, showed significantly less change in color relative to the hair prior to treatment.

Example 4 demonstrates that hair colored according to the disclosure, i.e. treated with a pretreatment composition according to the disclosure and subsequently dyed with a dyeing composition according to the disclosure, surprisingly and unexpectedly leads to enhanced color deposition and more vibrant hair colors compared to hair treated with a pretreatment composition not according to the disclosure, or hair not pre-treated as described herein.

Example 5—Methods of Altering the Color of Hair

The following combinations of pretreatment compositions according to Example 2 and dyeing compositions according to Example 3A were applied to swatches of hair:

| Example | | Pretreatment Composition | Dyeing Composition |
|---|---|---|---|
| Inventive | 5A | BTAC | HNT-AR33 (5.0%) |
| | 5B | CTAC | HNT-AR33 (5.0%) |
| | 5C | DTAC | HNT-AR33 (5.0%) |
| Comparative | 5D | Triton X-100 | HNT-AR33 (5.0%) |
| | 5E | None | HNT-AR33 (5.0%) |
| | 5F | CTAC mixed with HNT-AR33 (5.0%) | |

The process for Examples 5A-5D was as follows. First, the pretreatment composition was applied to swatches of 90% grey virgin hair at a ratio of 2 grams per 1 gram of hair and massaged through the hair to ensure maximum coverage. After a leave-in period of approximately 3 minutes, the pretreatment composition was removed from the hair by towel drying the hair. Subsequently, the dyeing composition was applied to the hair at a ratio of 2 grams per 1 gram of hair and massaged through the hair to ensure maximum coverage. After a leave-in period of approximately 30 minutes, the hair was rinsed with 10 passes of tap water (~37° C.). The hair was then dried, and the color change was evaluated.

For Example 5E (no pretreatment), the dyeing composition was applied to the hair at a ratio of 2 grams per 1 gram of hair and massaged through the hair to ensure maximum coverage. After a leave-in period of approximately 30 minutes, the hair was rinsed with 10 passes of tap water (~37° C.). The hair was then dried, and the color change was evaluated.

For Example 5F (pretreatment mixed with dyeing), 5% cetrimonium chloride and 5% of the Halloysite-Acid Red 33 composite were mixed in water, and the mixture was then applied to the hair at a ratio of 2 grams per 1 gram of hair and massaged through the hair to ensure maximum coverage. After a leave-in period of approximately 30 minutes, the hair was rinsed with 10 passes of tap water (~37° C.). The hair was then dried, and the color change was evaluated.

Figure 2:
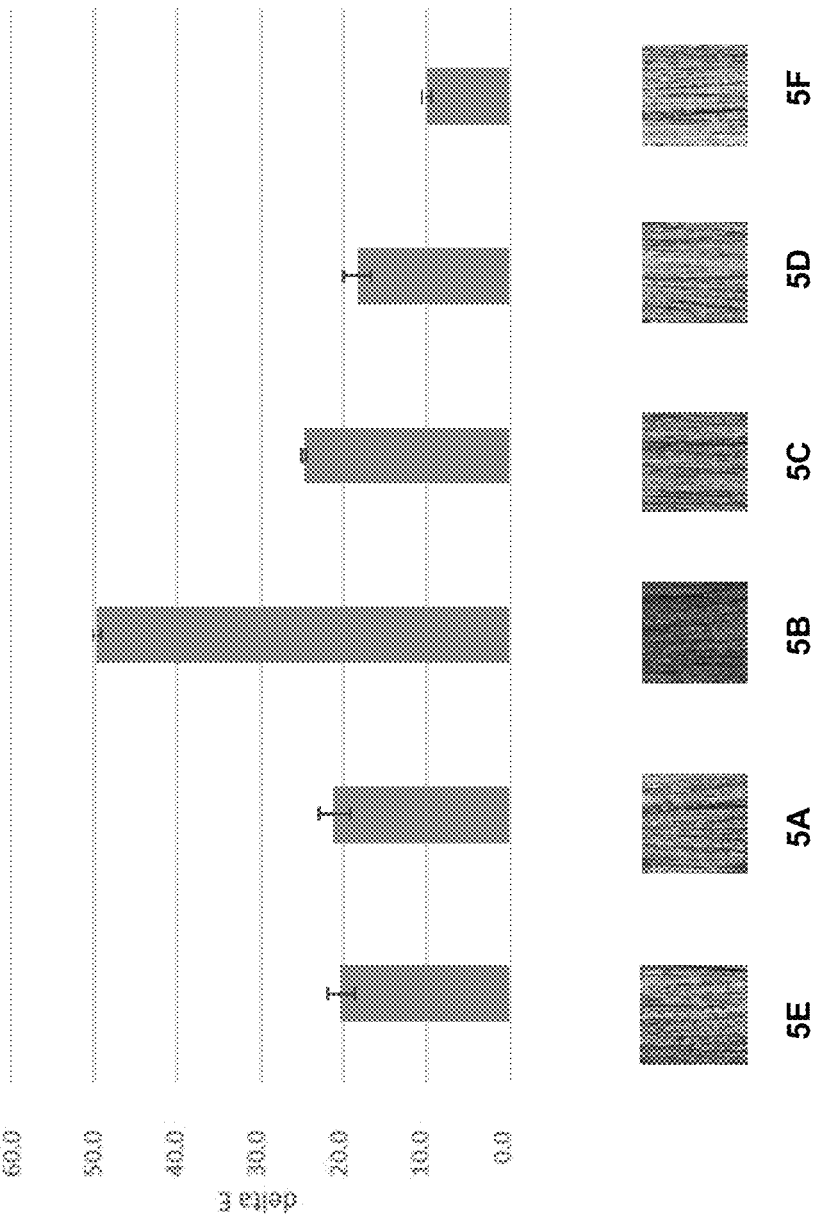
FIG. 2 is a graph demonstrating change in ΔE of hair treated according to methods of the disclosure with pretreatment compositions comprising cationic surfactants followed by dyeing compositions comprising microtube-dye composites, compared to hair treated with comparative methods, where Example 5B, having hair pretreated with a composition comprising cetyltrimethylammonium chloride followed by dyeing the hair with the halloysite-acid red 33 composite, showed the greatest enhancement in color deposition and vibrancy.

As seen in FIG. 2, the hair of inventive Examples 5A-5C shows the greatest change in ΔE (greatest color change) compared to the hair prior to treatment. Example 5B, having pretreated the hair with a composition comprising cetyltrimethylammonium chloride followed by dyeing the hair with the halloysite-dye composite, showed the greatest enhancement in color deposition and vibrancy. The hair of comparative Example 5D, following the same method but using a pretreatment composition not according to the disclosure, and the hair of comparative Example 5E, with no pretreatment step, showed significantly less change in color relative to the hair prior to treatment. The hair of comparative Example 5F had the least amount of change in color.

Like Example 4, Example 5 demonstrates that hair colored according to the disclosure, i.e. treated with a pretreatment composition according to the disclosure and subsequently dyed with a dyeing composition according to the disclosure, surprisingly and unexpectedly leads to enhanced color deposition and more vibrant hair colors compared to hair treated with a pretreatment composition not according to the disclosure, or hair not pre-treated as described herein. Example 5 further demonstrates that mixing a pretreatment composition with a dyeing composition does not achieve the same surprising and unexpected results as treating the hair with the pretreatment composition prior to dyeing.

Example 6—Methods of Altering the Color of Hair

The following combinations of pretreatment compositions according to Example 2 and dyeing compositions according to Examples 3A-3B were applied to swatches of hair in Examples 6A-6B. In Example 6C, no pretreatment composition was applied but the hair was dyed using the HNT-AR33 (5.0%) dyeing composition of Example 3A, and in Example 6D, no pretreatment composition was applied and the hair was dyed using a 0.28 wt % composition of Acid Red 33 (i.e. not as a composite).

| Example | | Pretreatment Composition | Dyeing Composition |
| --- | --- | --- | --- |
| Inventive | 6A | CTAC | HNT-AR33 (5.0%) |
| | 6B | CTAC | Acid Red 33 (0.28%) |
| Comparative | 6C | None | HNT-AR33 (5.0%) |
| | 6D | None | Acid Red 33 (0.28%) |

The process for Examples 6A-6B was as follows. First, the pretreatment composition was applied to swatches of 90% grey virgin hair at a ratio of 2 grams per 1 gram of hair and massaged through the hair to ensure maximum coverage. After a leave-in period of approximately 3 minutes, the pretreatment composition was removed from the hair by rinsing with water. Subsequently, the dyeing composition was applied to the hair at a ratio of 2 grams per 1 gram of hair and massaged through the hair to ensure maximum coverage. After a leave-in period of approximately 30 minutes, the hair was rinsed with 10 passes of tap water (~37° C.). The hair was then dried, and the color change was evaluated.

For Examples 6C-6D (no pretreatment), the dyeing composition was applied to the hair at a ratio of 2 grams per 1 gram of hair and massaged through the hair to ensure maximum coverage. After a leave-in period of approximately 30 minutes, the hair was rinsed with 10 passes of tap water (~37° C.). The hair was then dried, and the color change was evaluated.

Figure 3:
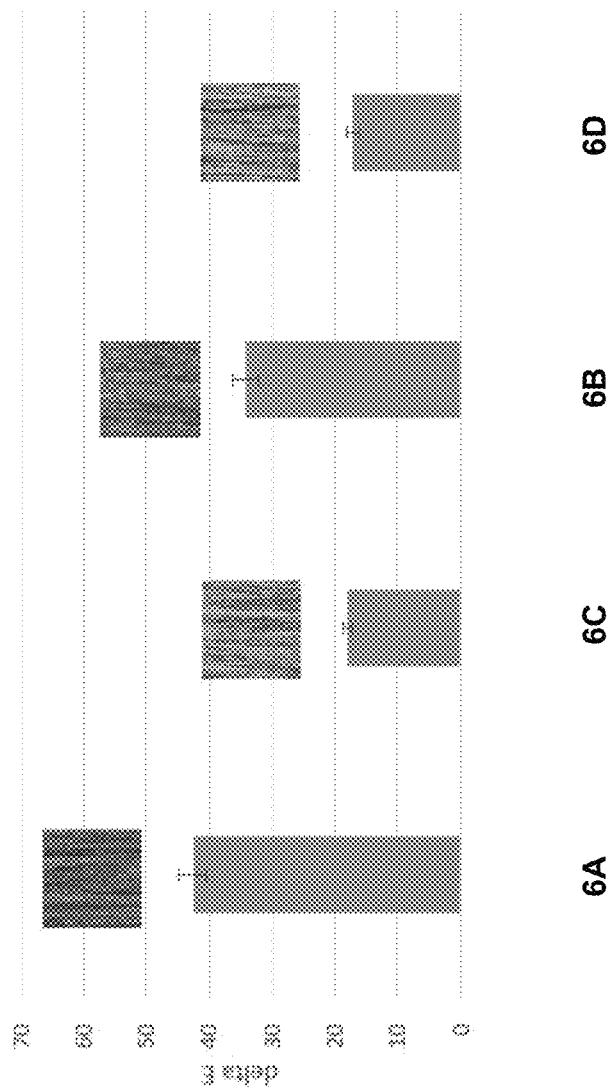
FIG. 3 is a graph demonstrating change in ΔE of hair treated according to methods of the disclosure with pretreatment compositions comprising cationic surfactants followed by dyeing compositions comprising either microtube-dye composites or the dye alone, compared to hair treated with comparative methods, where Example 6A, having hair pretreated with a composition comprising cetyltrimethylammonium chloride followed by dyeing the hair with the halloysite-acid red 33 composite, showed the greatest enhancement in color deposition and vibrancy.

As seen in FIG. 3, the hair of inventive Examples 6A-6B shows the greatest change in ΔE (greatest color change) compared to the hair prior to treatment. Example 6A, having pretreated the hair with a composition comprising cetyltrimethylammonium chloride followed by dyeing the hair with the halloysite-dye composite, showed the greatest enhancement in color deposition and vibrancy. The hair of comparative Examples 6C, with no pretreatment step, and comparative Example 6D, with no pretreatment step and not using a microtube-dye composite, showed significantly less change in color relative to the hair prior to treatment.

Example 6 demonstrates that hair colored according to the disclosure, i.e. treated with a pretreatment composition according to the disclosure and subsequently dyed with a dyeing composition according to the disclosure, surprisingly and unexpectedly leads to enhanced color deposition and more vibrant hair colors compared to hair not treated according to the disclosure, even when the concentration of composite in the dyeing composition was lower. Example 6 also demonstrates this improvement is seen whether the hair is dyed using a traditional hair dye composition (Example 6B) or a hair dye composition comprising a microtube-dye composite (Example 6A).

Figure 4:
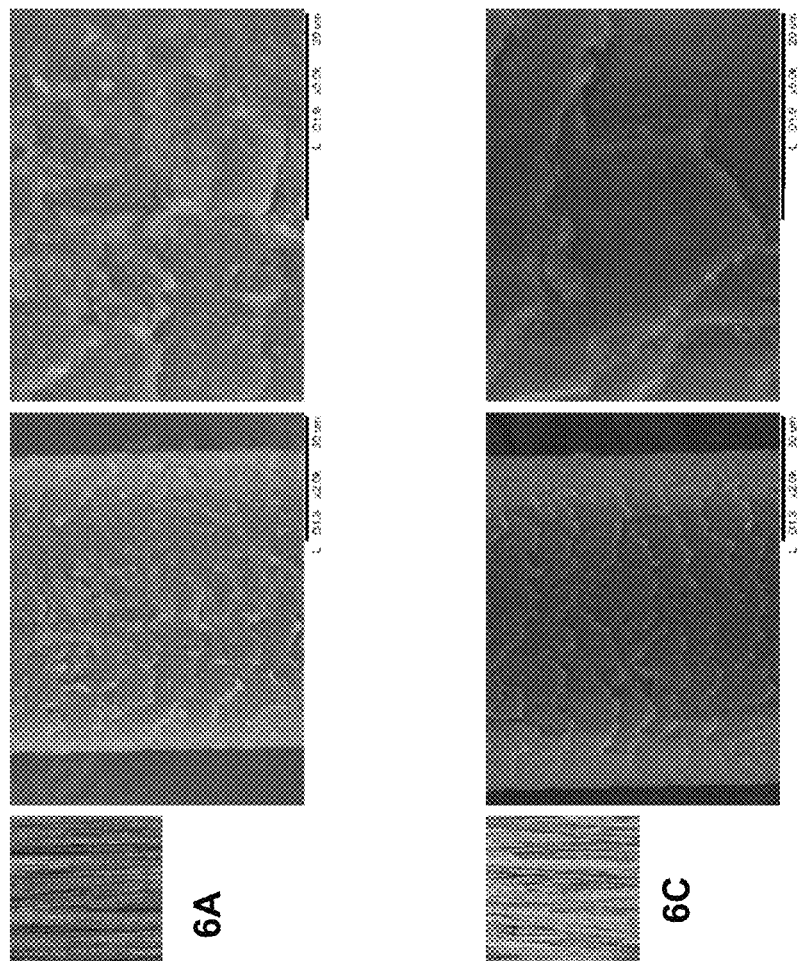
FIG. 4 shows images taken with a scanning electron microscope (SEM) of halloysite-acid red 33 composites on hair fibers treated according to methods of the disclosure and comparative methods, where the hair in Example 6A, pretreated with a composition comprising cetyltrimethylammonium chloride followed by dyeing the hair with the halloysite-dye composite, showed greater deposition of microtube-dye composites on the hair fiber than the hair of Example 6C without pretreatment.

FIG. 4 shows SEM images of hair fibers treated in accordance with Example 6A (top) and 6C (bottom), at magnifications of 2000× (left side) and 5000× (right side). The HNT-AR33 composites are visible at significantly greater concentration on the hair fiber of Example 6A than that of 6C. The SEM images thus confirm that the methods of altering the color of hair according to the disclosure lead to greater deposition of microtube-dye composites on the hair fibers, which provides the observed enhanced change in ΔE for hair treated according to the disclosure.

Example 7—Methods of Altering the Color of Hair

The following combinations of pretreatment compositions according to Example 2 and dyeing compositions according to Example 3A were applied to swatches of hair:

| Example | | Pretreatment Composition | Dyeing Composition |
| --- | --- | --- | --- |
| Inventive | 7A | BTAC | HNT-AB1 (5.0%) |
| | 7B | CTAC | HNT-AB1 (5.0%) |
| | 7C | DTAB | HNT-AB1 (5.0%) |
| Comparative | 7D | Triton X-100 | HNT-AB1 (5.0%) |
| | 7E | None | HNT-AB1 (5.0%) |

The process for Examples 7A-7D was as follows. First, the pretreatment composition was applied to swatches of 90% grey virgin hair at a ratio of 2 grams per 1 gram of hair and massaged through the hair to ensure maximum coverage. After a leave-in period of approximately 3 minutes, the pretreatment composition was removed from the hair by towel drying. Subsequently, the dyeing composition was applied to the hair at a ratio of 2 grams per 1 gram of hair and massaged through the hair to ensure maximum coverage. After a leave-in period of approximately 30 minutes, the hair was rinsed with 10 passes of tap water (~37° C.). The hair was then dried, and the color change was evaluated.

For Example 7E (no pretreatment), the dyeing composition was applied to the hair at a ratio of 2 grams per 1 gram of hair and massaged through the hair to ensure maximum coverage. After a leave-in period of approximately 30 minutes, the hair was rinsed with 10 passes of tap water (~37° C.). The hair was then dried, and the color change was evaluated.

Figure 5:
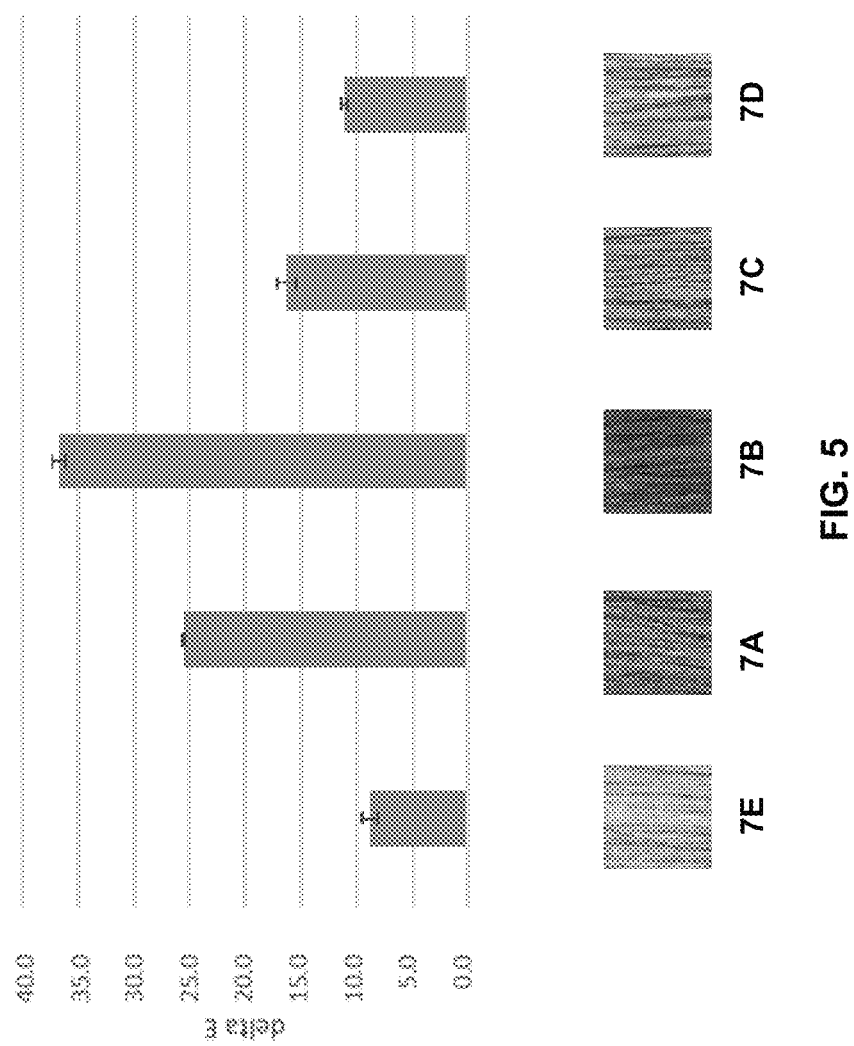
FIG. 5 is a graph demonstrating change in ΔE of hair treated according to methods of the disclosure with pretreatment compositions comprising cationic surfactants followed by dyeing compositions comprising microtube-dye composites, compared to hair treated with comparative methods, where Example 7B, having hair pretreated with a composition comprising cetyltrimethylammonium chloride followed by dyeing the hair with the halloysite-acid black 1 composite, showed the greatest enhancement in color deposition and vibrancy.

As seen in FIG. 5, the hair of inventive Examples 7A-7C shows the greatest change in ΔE (greatest color change) compared to the hair prior to treatment. Example 7B, having pretreated the hair with a composition comprising cetyltrimethylammonium chloride followed by dyeing the hair with the halloysite-dye composite, showed the greatest enhancement in color deposition and vibrancy. The hair of comparative Example 7D, following the same method but using a pretreatment composition not according to the disclosure, and the hair of comparative Example 7E, with no pretreatment step, showed significantly less change in color relative to the hair prior to treatment.

Example 7 demonstrates that hair colored according to the disclosure, i.e. treated with a pretreatment composition according to the disclosure and subsequently dyed with a dyeing composition according to the disclosure, surprisingly and unexpectedly leads to enhanced color deposition and more vibrant hair colors compared to hair treated with a pretreatment composition not according to the disclosure, or hair not pre-treated as described herein. Example 7 shows that the same benefit is achieved with different anionic dyes.

Example 8—Methods of Altering the Color of Hair

The following combinations of pretreatment compositions according to Example 2 and dyeing compositions according to Example 3C were applied to swatches of hair:

| Example | | Pretreatment Composition | Dyeing Composition |
|---|---|---|---|
| Inventive | 8A | CTAC | HNT-CCM (0.5%) |
|  | 8B | CTAC | HNT-CCM (5.0%) |
| Comparative | 8C | None | HNT-CCM (5.0%) |

The process for Examples 8A-8B was as follows. First, the pretreatment composition was applied to swatches of 90% grey virgin hair at a ratio of 2 grams per 1 gram of hair and massaged through the hair to ensure maximum coverage. After a leave-in period of approximately 3 minutes, the pretreatment composition was removed from the hair by rinsing with water. Subsequently, the dyeing composition was applied to the hair at a ratio of 2 grams per 1 gram of hair and massaged through the hair to ensure maximum coverage. After a leave-in period of approximately 30 minutes, the hair was rinsed with 10 passes of tap water (~37° C.). The hair was then dried, and the color change was evaluated.

For Example 8C (no pretreatment), the dyeing composition was applied to the hair at a ratio of 2 grams per 1 gram of hair and massaged through the hair to ensure maximum coverage. After a leave-in period of approximately 30 minutes, the hair was rinsed with 10 passes of tap water (~37° C.). The hair was then dried, and the color change was evaluated.

Figure 6:
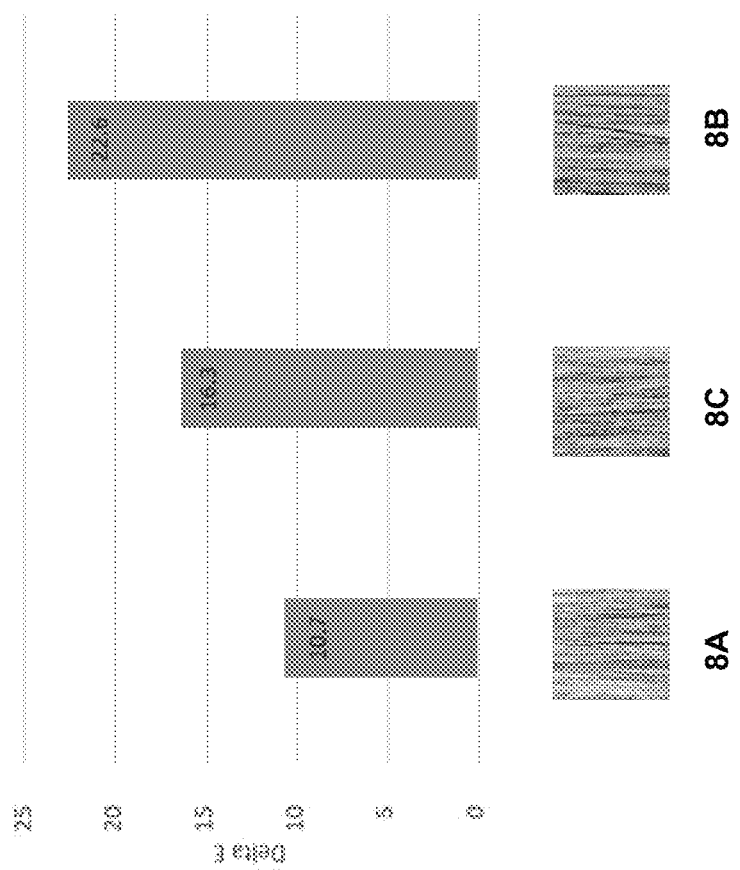
FIG. 6 is a graph demonstrating change in ΔE of hair treated according to methods of the disclosure with pretreatment compositions comprising cationic surfactants followed by dyeing compositions comprising microtube-dye composites, compared to hair treated with comparative methods, where Example 8B, having hair pretreated with a composition comprising cetyltrimethylammonium chloride, followed by dyeing the hair with the halloysite-curcumin composite at 5 wt %, shows the greatest change in ΔE compared to the hair prior to treatment.

As seen in FIG. 6, the hair of inventive Example 8B, having pretreated the hair with a composition comprising cetyltrimethylammonium chloride, followed by dyeing the hair with the halloysite-dye composite at 5 wt %, shows the greatest change in ΔE (greatest color change) compared to the hair prior to treatment. The hair of comparative Example 8C, with no pretreatment step, showed significantly less change in color relative to the hair prior to treatment compared to Example 8B which had the same dye load.

As also see in FIG. 6, although Example 8A, having pretreated the hair with a composition comprising cetyltrimethylammonium chloride, followed by dyeing the hair with the halloysite-dye composite at 0.5 wt %, showed a lower ΔE than either Examples 8B (22.6) or 8C (16.3), the ΔE (10.7) nevertheless demonstrates that a meaningful difference in color can be achieved even at low concentrations of microtube-dye composites when hair is dyed using methods according to the disclosure.

Example 8 demonstrates that hair colored according to the disclosure, i.e. treated with a pretreatment composition according to the disclosure and subsequently dyed with a dyeing composition according to the disclosure, surprisingly and unexpectedly leads to enhanced color deposition and more vibrant hair colors compared to hair not pre-treated as described herein, even at low concentrations. Example 8 shows that the same benefit is achieved with neutral dyes, including natural dyes.

Example 9—Pretreatment With Shampoo Containing Anionic Surfactants

Hair was washed using a standard shampoo containing approximately 11 wt % of a mixture of anionic surfactants (disodium laureth sulfosuccinate, sodium cocoyl isethionate, sodium lauryl sulfoacetate, and sodium lauryl sarcosinate) and non-ionic surfactants. The hair was rinsed, and the HNT-AR33 (5.0%) dyeing composition of Example 3A was applied to the hair. After a leave-in period of approximately 30 minutes, the hair was rinsed with 10 passes of tap water (~37° C.). The hair was then dried, and the color change was evaluated.

Relative to the color of the hair before shampooing and treating with the dyeing composition, the color of the hair after treatment was substantially unchanged.

The above examples demonstrate that the systems, methods, and kits according to the disclosure surprisingly and unexpectedly provide improved color deposition to hair relative to those not according to the disclosure.

The invention claimed is:

1. A method of altering the color of hair comprising:
    (a) applying to the hair a pretreatment composition comprising at least one cationic surfactant and at least one solvent, and
    (b) applying to the hair a dyeing composition comprising at least one microtube-dye composite and at least one solvent,
        wherein, in the microtube-dye composite, the dye comprises at least one anionic or neutral hair dyeing agent.

2. The method according to claim 1, wherein the at least one cationic surfactant is chosen from quaternary ammonium salts of formula (I):

wherein R1 to R4, which may be identical or different, are chosen from a linear or branched aliphatic group comprising from 1 to 30 carbon atoms or an aromatic group, wherein at least one of the groups R1 to R4 comprise from 12 to 22 carbon atoms, and X$^-$ is an anionic counterion chosen from halides.

3. The method according to claim 1, wherein the at least one cationic surfactant is chosen from alkyltrimethylammonium chlorides in which the alkyl group contains from 12 to 22 carbon atoms.

4. The method according to claim 1, wherein the pretreatment composition is an aqueous composition comprising a total amount of cationic surfactant ranging from about 0.001% to about 25% by weight, relative to the total weight of the pretreatment composition.

5. The method according to claim 1, wherein the microtube-dye composite comprises a halloysite-dye composite comprising at least one anionic or neutral hair dyeing agent.

6. The method according to claim 1, wherein the at least one anionic hair dyeing agent is chosen from acidic nitro direct dyes, acidic azo dyes, acidic azine dyes, acidic triarylmethane dyes, acidic indoamine dyes, acidic anthraquinone dyes, indigoid dyes, acidic natural dyes, and combinations thereof.

7. The method according to claim 1, wherein the dyeing composition is an aqueous composition comprising a total amount of microtube-dye composite ranging from about 0.01% to about 15% by weight, relative to the total weight of the dyeing composition.

8. The method according to claim 1, wherein the pretreatment composition is removed from the hair before the dyeing composition is applied.

9. The method according to claim 1, comprising:
    (a) applying to the hair a pretreatment composition comprising water and at least one cationic surfactant chosen from alkyltrimethylammonium chlorides in which the alkyl group contains from 12 to 22 carbon atoms,
(b) leaving the pretreatment composition on the hair for a leave-in period ranging from about 30 seconds to about 10 minutes,
(c) optionally, removing the pretreatment composition from the hair,
(d) applying to the hair a dyeing composition comprising water and at least one halloysite-dye composite, wherein in the halloysite-dye composite, the dye comprises at least one anionic or neutral hair dyeing agent,
(e) leaving the dyeing composition on the hair for a leave-in period ranging from about 1 minute to about 45 minutes, and
(f) rinsing the dyeing composition from the hair.

10. A system for altering the color of hair comprising:
(a) a pretreatment composition comprising at least one cationic surfactant and at least one solvent, and
(b) a dyeing composition comprising at least one microtube-dye composite and at least one solvent,
wherein, in the microtube-dye composite, the dye comprises at least one anionic or neutral hair dyeing agent.

11. The system according to claim 10, wherein the at least one cationic surfactant is chosen from quaternary ammonium salts of formula (I):

wherein R1 to R4, which may be identical or different, are chosen from a linear or branched aliphatic group comprising from 1 to 30 carbon atoms or an aromatic group, wherein at least one of the groups R1 to R4 comprise from 12 to 22 carbon atoms, and
X⁻ is an anionic counterion chosen from halides.

12. The system according to claim 10, wherein the at least one cationic surfactant is chosen from alkyltrimethylammonium chlorides in which the alkyl group contains from 12 to 22 carbon atoms.

13. The system according to claim 10, wherein the pretreatment composition is an aqueous composition comprising a total amount of cationic surfactant ranging from about 0.001% to about 25% by weight, relative to the total weight of the pretreatment composition.

14. The system according to claim 10, wherein in the microtube-dye composite, the microtube comprises halloysite.

15. The system according to claim 10, wherein the at least one anionic hair dyeing agent is chosen from acidic nitro direct dyes, acidic azo dyes, acidic azine dyes, acidic triarylmethane dyes, acidic indoamine dyes, acidic anthraquinone dyes, indigoid dyes, acidic natural dyes, and combinations thereof.

16. The system according to claim 10, wherein the dyeing composition is an aqueous composition comprising a total amount of microtube-dye composite ranging from about 0.01% to about 15% by weight, relative to the total weight of the dyeing composition.

17. A kit for altering the color of hair comprising:
(a) a first compartment or container comprising a pretreatment composition comprising at least one cationic surfactant and at least one solvent, and
(b) a second compartment or container comprising a dyeing composition comprising at least one microtube-dye composite and at least one solvent,
wherein, in the microtube-dye composite, the dye comprises at least one anionic or neutral hair dyeing agent.

18. The kit according to claim 17, wherein the at least one cationic surfactant is chosen from quaternary ammonium salts of formula (I):

wherein R1 to R4, which may be identical or different, are chosen from a linear or branched aliphatic group comprising from 1 to 30 carbon atoms or an aromatic group, wherein at least one of the groups R1 to R4 comprise from 12 to 22 carbon atoms, and
X⁻ is an anionic counterion chosen from halides.

19. The kit according to claim 17, wherein the at least one cationic surfactant is chosen from alkyltrimethylammonium chlorides in which the alkyl group contains from 12 to 22 carbon atoms.

20. The kit according to claim 17, wherein the pretreatment composition is an aqueous composition comprising a total amount of cationic surfactant ranging from about 0.001% to about 25% by weight, relative to the total weight of the pretreatment composition.

21. The system according to claim 10, wherein in the microtube-dye composite, the microtube comprises halloysite.

22. The kit according to claim 17, wherein the at least one anionic hair dyeing agent is chosen from acidic nitro direct dyes, acidic azo dyes, acidic azine dyes, acidic triarylmethane dyes, acidic indoamine dyes, acidic anthraquinone dyes, indigoid dyes, acidic natural dyes, and combinations thereof.

23. The kit according to claim 17, wherein the dyeing composition is an aqueous composition comprising a total amount of microtube-dye composite ranging from about 0.01% to about 15% by weight, relative to the total weight of the dyeing composition.

* * * * *